US005876335A

United States Patent [19]

Handy et al.

[11] Patent Number: 5,876,335

[45] Date of Patent: Mar. 2, 1999

[54] MULTIPURPOSE PREGNANCY AND LABOR TIMING DEVICE

[75] Inventors: Jeffrey D. Handy, Collierville, Tenn.; Mark J Lloyd, Cary, N.C.

[73] Assignee: J.D.H. Enterprises, Inc., Gainesville, Fla.

[21] Appl. No.: 808,747

[22] Filed: Feb. 28, 1997

[51] Int. Cl.[6] .............................. G04B 19/06; A61B 5/11

[52] U.S. Cl. .............................. 600/304

[58] Field of Search .............................. 600/300, 587, 600/304, 591; 128/897

[56] References Cited

U.S. PATENT DOCUMENTS

| | | | |
|---|---|---|---|
| 4,047,010 | 9/1977 | Perotto et al. | 7/38 |
| 4,493,043 | 1/1985 | Forbath | 15/20 |
| 4,497,312 | 2/1985 | Byrd | 19/6 |
| 4,711,585 | 12/1987 | Fresquez, et al. . | |
| 5,042,503 | 8/1991 | Torok et al. | 600/587 |

FOREIGN PATENT DOCUMENTS

| | | | |
|---|---|---|---|
| 2193015 | 1/1988 | United Kingdom | 368/109 |

*Primary Examiner*—John P. Lacyk
*Assistant Examiner*—Samuel Gilbert
*Attorney, Agent, or Firm*—Walker, McKenzie & Walker, P.C.

[57] ABSTRACT

A multipurpose pregnancy and labor timing device for use by expectant parents during the gestation, labor, and birth of their child. The timing device includes an output device for conveying a plurality of datum to a human ovserver. The datum conveyed may represent a current time, day and date, an expected date of birth of the child, an estimated elapsed time period since the conception date of the child, an estimated time period until the birth of the child, the count of contractions experienced by a woman undergoing the process of labor, the time interval between contractions, the duration of a contraction, and the actual time and date of the birth of the child. The timing device also includes a non-volatile memory for storing at least some of the plurality of datum, a data selection device for selecting at least some of the plurality of datum for conveyance by the output device, and a data initialization device for initializing the first datum and the second datum. The timing device further includes a processor control device for performing a first sequence of operations to store at least some of the plurality of datum into the nonvolatile memory, for performing a second sequence of operations to retrieve at least some of the plurality of datum from the nonvolatile memory so that at least some of the plurality of datum is conveyed by the output device, and for calculating at least some of the plurality of datum.

2 Claims, 29 Drawing Sheets

Microfiche Appendix Included
(1 Microfiche, 57 Pages)

ORGANIZATION
OF FIGURES

ORGANIZATION
OF FIGURES

ORGANIZATION OF FIGURES

MULTIPURPOSE PREGNANCY AND LABOR TIMING DEVICE

CROSS REFERENCE TO RELATED APPLICATIONS

Not applicable.

STATEMENT REGARDING FEDERALLY SPONSORED RESEARCH OR DEVELOPMENT

Not applicable.

REFERENCE TO A MICROFICHE APPENDIX

A microfiche appendix consisting of a single fiche showing a 57-page computer program is included as a part of this application.

BACKGROUND OF THE INVENTION

1. Field of the Invention

The present invention relates, in general, to a medical device, and in particular, to a multipurpose pregnancy and labor timing device for assisting a pregnant woman and a prospective father in keeping track of the expected time until the birth of their child, for timing contractions when the woman is experiencing labor, and for recording the exact time and date of birth of their child.

2. Information Disclosure Statement

While contraction timers are well-known in the art, none of the prior art discloses a multipurpose pregnancy and labor timing device for assisting a pregnant woman and prospective father in keeping track of the expected time until the birth of their child, for timing contractions when the woman is experiencing labor, and also for recording the exact time and date of birth of their child.

A preliminary patentability search produced the following patents, some of which may be relevant to the present invention: Fresquez et al., U.S. Pat. No. 4,711,585, issued Dec. 8, 1987; Byrd, U.S. Pat. No. 4,497,312, issued Feb. 5, 1985; Forbath, U.S. Pat. No. 4,493,043, issued Jan. 8, 1985; and Perotto et al., U.S. Pat. No. 4,047,010, issued Sep. 6, 1977. None of these references, either singly or in combination, disclose or suggest the present invention.

BRIEF SUMMARY OF THE INVENTION

The present invention is a multipurpose pregnancy and labor timing device which can be used to aid expectant parents during the gestation, labor, and birth of their child. The multipurpose pregnancy and labor timing device comprises output means for conveying a plurality of datum to an observer. The plurality of datum includes a first datum representing a current time and date and a second datum that is a fixed function of a selected conception date of the child. The second datum can represent, for example, the expected date of birth of the child. The plurality of datum may include other datum representing, for example, an estimated elapsed time period since the conception date of the child, an estimated time period until the birth of the child, the count of contractions experienced by a woman undergoing the process of labor, the time interval between contractions, the duration of a contraction, and the actual time and date of the birth of the child. The multipurpose pregnancy and labor timing device also comprises nonvolatile memory means for storing at least some of the plurality of datum, data selection means for selecting at least some of the plurality of datum for conveyance by output means, and data initialization means for initializing the first datum and the second datum. The multipurpose pregnancy and labor timing device further comprises processor control means for performing a first sequence of operations to store at least some of the plurality of datum into the nonvolatile memory means, for performing a second sequence of operations to retrieve at least some of the plurality of datum from the nonvolatile memory means so that at least some of the plurality of datum is conveyed by output means, and for calculating at least some of the plurality of datum.

It is an object of the present invention to provide a multipurpose pregnancy and labor timer which displays a current time, day and date.

It is an additional object of the present invention to provide a multipurpose pregnancy and labor timer which displays an expected date of birth of a child.

It is an additional object of the present invention to provide a multipurpose pregnancy and labor timer which displays an elapsed time period since a conception of a child.

It is an additional object of the present invention to provide a multipurpose pregnancy and labor timer which displays an estimated time period until the birth of a child.

It is an additional object of the present invention to provide a multipurpose pregnancy and labor timer which displays the count of contractions occurring during labor.

It is an additional object of the present invention to provide a multipurpose pregnancy and labor timer which displays the time interval between the contractions.

It is an additional object of the present invention to provide a multipurpose pregnancy and labor timer which displays the duration of the contraction.

It is a further object of the present invention to provide a multipurpose pregnancy and labor timer which records and displays the time and date of the birth of a child.

It is a further object of the present invention to provide a multipurpose pregnancy and labor timer which includes a data interface for transmitting data to an external data device.

It is a further object of the present invention to provide a multipurpose pregnancy and labor timer which includes an audible tone generator.

DETAILED DESCRIPTION OF THE INVENTION

Figure 1:
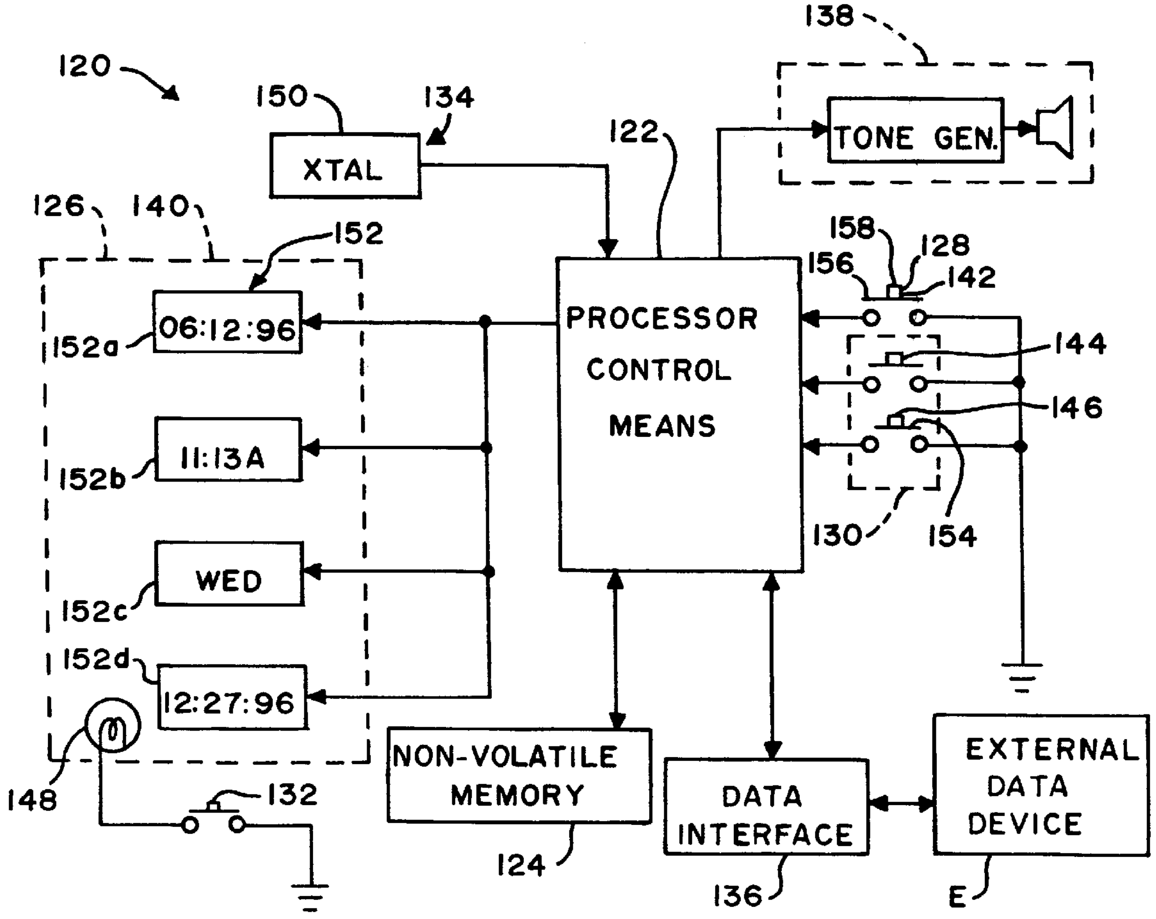
FIG. 1 is an electronic schematic, in block diagram format, of the present invention.

Referring to FIG. 1, an electronic schematic in block diagram format, the present invention is seen to comprise a multipurpose pregnancy and labor timing device 120 which can be used to aid expectant parents during the pregnancy and labor of their child. The multipurpose pregnancy and labor timing device 120 is seen to comprise output means 126 for conveying a plurality of datum to a human being. Output means 126 comprises a well-known device for visually conveying the plurality of datum to an observer such as a human parent, and preferably comprises an alpha-numeric display 140 having readouts 152, e.g., readouts 152*a*, 152*b*, 152*c*, and 152*d*, for simultaneous display of some of the plurality of datum. It should be understood, however, that the alpha-numeric display 140 is not limited to only having four readouts 152 as shown, but that some of readouts 152*a*, 152*b*, 152*c*, or 152*d* may perform multiple functions. Each readout 152 is capable of simultaneously displaying multiple alpha-numeric characters. The alpha-numeric display 140 has a plurality of display modes, and certain pre-selected datums of the plurality of datum can be displayed in the readouts 152 in each one of the display modes. The alpha-numeric display 140 may comprise a liquid crystal display or a light emitting diode but preferably comprises a liquid crystal display. The multipurpose pregnancy and labor timing device 120 preferably includes a light 148 operated by light switch 132 so that the liquid crystal display can be read in the dark.

The plurality of datum includes a first datum representing a current time and date and preferably also represents a current day of the week. The plurality of datum also includes a second datum that is a fixed function of a selected conception date of a child. The second datum may represent the estimated conception date of the child but preferably represents the expected date of birth of the child. The expected date of birth of the child will typically be estimated by the expectant mother's physician. The plurality of datum preferably includes other datum such as a third datum representing an estimated elapsed time period since the conception date of the child, a fourth datum representing an estimated time period until the birth of the child, a fifth datum representing the count of contractions experienced by a woman undergoing the process of labor, a sixth datum representing the time interval between contractions, a seventh datum representing the duration of a contraction, and an eighth datum representing the actual time and date of the birth of the child.

The multipurpose pregnancy and labor timing device 120 comprises nonvolatile memory means 124 for storing at least some of the plurality of datum. The multipurpose pregnancy and labor timing device 120 further comprises processor control means 122 for performing a first sequence of operations to store at least some of the plurality of datum into nonvolatile memory means 124, for performing a second sequence of operations to retrieve at least some of the plurality of datum from nonvolatile memory means 124 so that at least some of the plurality of datum is conveyed to a human observer by output means 126, and for calculating at least some of the plurality of datum. Processor control means 122 may be implemented by a variety of technologies, well-known to those skilled in the art, but is preferably implemented by a well-known microprocessor chip. Nonvolatile memory means 124 preferably includes a well-known random access memory device for storing some of the plurality of datum and a well known read-only memory device for storing software commands to control the operation of processor control means 122. Nonvolatile memory means 124 may alternatively include a random access memory device coupled with a fool-proof dual battery or may include other suitable memory devices as will now be apparent to those skilled in the art. Processor control means 122 preferably counts pulses having a relatively stable repetition rate in order to calculate and maintain the first datum representing the current time and date. Such pulses are produced by a tick generator 134 which preferably includes a well-known crystal oscillator circuit 150.

The multipurpose pregnancy and labor timing device 120 further comprises data selection means 128 for selecting at least some of the plurality of datum for conveyance to a human observer by output means 126. As previously described, output means 126 preferably comprises the alpha-numeric display 140 having a plurality of display modes so that certain pre-selected datums of the plurality of datum can be displayed in each one of the display modes. Data selection means 128 preferably includes mode selection means 158 for selecting one of the plurality of display modes. Mode selection means 158 preferably includes a push-button mode switch 142 for sending a stimulus to processor control means 122. Upon receiving the stimulus, processor control means 122 will perform a sequence of operations, defined as a second sequence of operations, to retrieve at least some of the plurality of datum from nonvolatile memory means 124 and cause the alpha-numeric display 140 to enter into a different one of the plurality of display modes.

The alpha-numeric display 140 preferably has four different display modes. In a first display mode (the "CURRENT & DUE MODE"), the alpha-numeric display 140 preferably displays the first datum and the second datum. The first datum is preferably displayed using three of the readouts 152. One readout, preferably readout 152*b*, shows the current time in hours, minutes and seconds. Another readout, preferably readout 152*a*, shows the current date as the current month, the current day of the month and the current year, and a third readout, preferably readout 152*c*, shows the current day of the week. The second datum is preferably displayed using a single readout, preferably readout 152*d*, and shows the month, day of the month, and year of the estimated date of birth of the child.

The multipurpose pregnancy and labor timing device 120 further comprises data initialization means 130 for initializing the first datum and the second datum. Data initialization means 130 may be implemented by a variety of well-known electronic circuits but preferably comprises an electronic circuit including a push-button set switch 144 and a push-button increment switch 146. Data initialization means 130 is preferably constructed so that when the alpha-numeric display 140 is in the first display mode, pushing set switch 144 twice in a row will send a stimulus to processor control means 122, and processor control means 122 will cause the multipurpose pregnancy and labor timing device 120 to enter an initialization mode. When in the initialization mode, one or more characters representing part of the first or the second datum will blink on and off indicating the particular part of the first or second datum which is enabled to be initialized. Each time set switch 144 is pressed, one or more other characters will blink on and off indicating that a different part of the first datum or the second datum is enabled to be initialized. Pressing increment switch 146 will cause the enabled part of the first or second datum to increment to a desired value. Increment switch 146 can be held down or continually pressed until the enabled part of the datum is incremented to the desired value. After each part of the first and second datum has been initialized, pressing the set switch 144 one more time cause the multipurpose pregnancy and labor timing device 120 to exit the initialization mode and the characters will cease to blink on and off.

In a second display mode (the "PREGNANCY MODE"), the alpha-numeric display 140 preferably displays the third datum and the fourth datum. The third datum and the fourth datum are preferably displayed using two of the readouts 152 for each datum. The third datum is displayed showing the estimated elapsed number of weeks and days in one readout, preferably readout 152*a*, and showing the estimated elapsed number of hours, minutes and seconds in another readout, preferably readout 152*b*. The fourth datum is displayed showing the number of weeks and days until the estimated time and date of birth of the child in one readout, preferably readout 152*c*, and showing the estimated number of hours, minutes and seconds until the estimated time and date of birth of the child in another readout, preferably readout 152*d*.

In a third display mode (the "LABOR MODE"), the alpha-numeric display 140 preferably displays the first datum, the fifth datum, the sixth datum and the seventh datum. In the third display mode, each datum is displayed using a different single readout 152. The first datum is displayed showing the current hour, minute and second, preferably using readout 152*b*. The fifth datum is displayed showing the count of contractions, preferably using readout 152*a*. The sixth datum is displayed showing the number of minutes and seconds between contractions, preferably using readout 152*c*. The seventh datum is displayed showing the duration of the contraction in minutes and seconds, preferably using readout 152*d*.

The multipurpose pregnancy and labor timing device 120 preferably includes signaling means 154 for entering into nonvolatile memory means 124 both a first event representing a start time of a contraction and a second event representing a stop time of a contraction. Processor control means 122 then calculates the fifth datum as a function of at least one of the first and second events, and processor control means 122 calculates the sixth datum and the seventh datum as a function of both of the first and second events. Signaling means 154 is preferably implemented by a well-known electronic circuit which includes push-button increment switch 146 such that a stimulus is sent to processor control means 122 each time increment switch 146 is depressed. Signaling means 154 is preferably constructed so that, when the alpha-numeric display 140 is in the third display mode, processor control means 122 and signaling means 154 will operate in the following manner. Processor control means 122 will increment the fifth datum, which represents the count of contractions, every other time increment switch 146 is pushed, i.e., each time a contraction duration begins to be timed, in a manner hereinafter described. Processor control means 122 starts to increment the seventh datum, which represents the duration of a contraction, when increment switch 146 is pushed for the first time. When increment switch 146 is pushed a second time, processor control means 122 stops incrementing the seventh datum and starts incrementing the sixth datum, which represents the time interval between contractions. When increment switch 146 is pushed a third time, processor control means 122 resets the seventh datum and again starts to increment the seventh datum. When increment switch 146 is pushed a fourth time, processor control means 122 stops incrementing the seventh datum, resets the sixth datum and starts incrementing the sixth datum. The multipurpose pregnancy and labor timing device 120 continues to operate in this manner, while the alpha-numeric display 140 is in the third display mode.

While in the third display mode (the "LABOR MODE"), the internal operation of the multipurpose pregnancy and labor timing device 120 is similar to the operation of the device disclosed in Forbath, U.S. Pat. No. 4,493,043, issued Jan. 8, 1985, which is fully incorporated herein by reference.

The multipurpose pregnancy and labor timing device 120 may include a data interface 136 operatively connected to nonvolatile memory means 124 and for transmitting at least one of the plurality of datum to an external data device E. Data interfaces are well-known to those skilled in the art and data interface 136 can be implemented by any one of a number of well-known electronic circuits. The data interface 136 is preferably constructed so that the data interface 136 can transmit the fifth, sixth, and seventh datum to an external data device E. The external device B can then supply information about the contractions to a medical professional who can use the information to assist in the delivery of the child.

In the fourth display mode (the "BIRTHDAY & DUE MODE"), the alpha-numeric display 140 preferably displays the eighth datum and may display the second datum. The eighth datum is displayed using three of the readouts 152. One readout, preferably readout 152*a*, shows the month, day of the month and year of the actual date of birth of the child. Another readout, preferably readout 152*c*, shows the day of the week of the actual date of birth of the child. A third readout, preferably readout 152*b*, shows the hour, the number of minutes and the number of seconds of the actual time of birth of the child. The second datum is displayed using a single readout, preferably readout 152*d*, showing the month, day of the month and year of the originally-estimated date of birth of the child so that the parent(s) can compare the actual birth date with the previously-expected birth date.

The multipurpose pregnancy and labor timing device 120 preferably includes entering means 156 for entering the eighth datum into nonvolatile memory means 124. Entering means 156 is preferably constructed to include the mode switch 142 so that, when pressed, the mode switch 142 sends a stimulus to processor control means 122. Processor control means 122 will then copy the current first datum into the eighth datum and cause the alpha-numeric display 140 to enter the fourth display mode.

Figure 2:
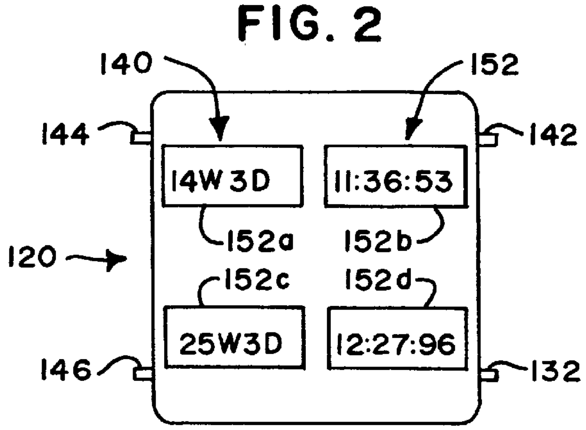
FIG. 2 is a front view of the present invention showing output means comprising an alpha-numeric display for conveying a plurality of datum to a human being.
Figure 3A:
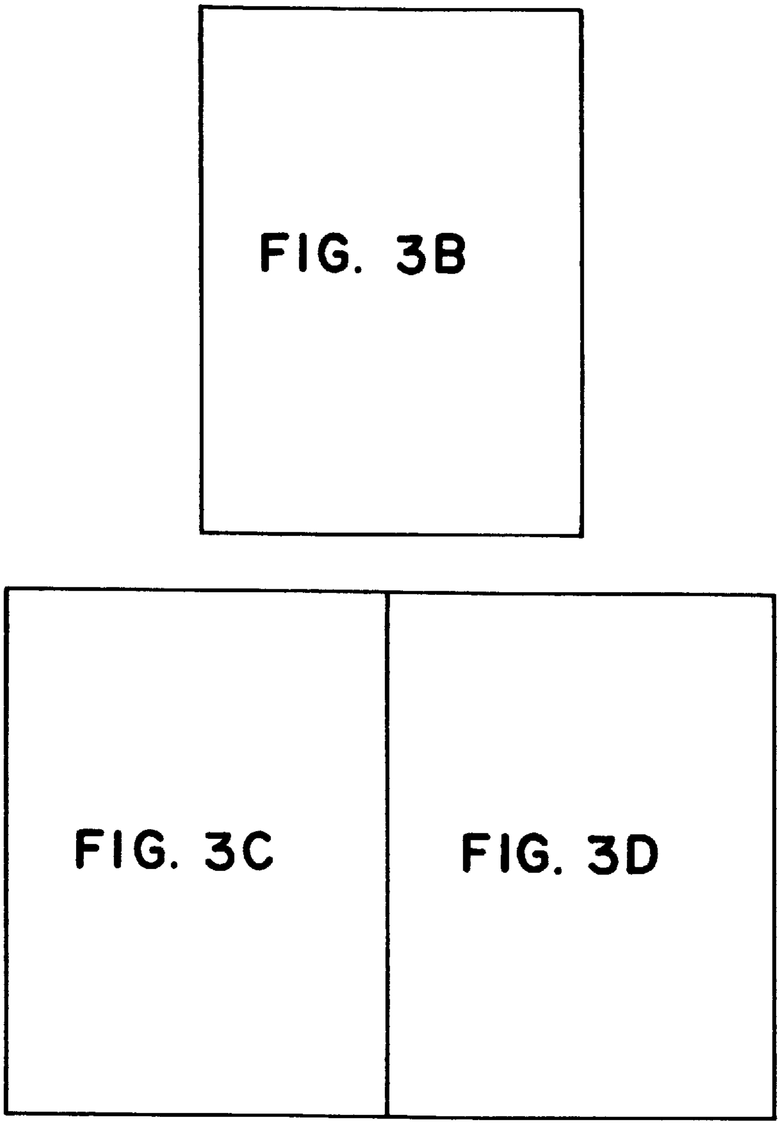
FIG. 3A shows the organization of FIGS. 3B, 3C, and 3D, which together represent, as an object information model, a flow diagram showing a preferred operation of the present invention.
Figure 3B:
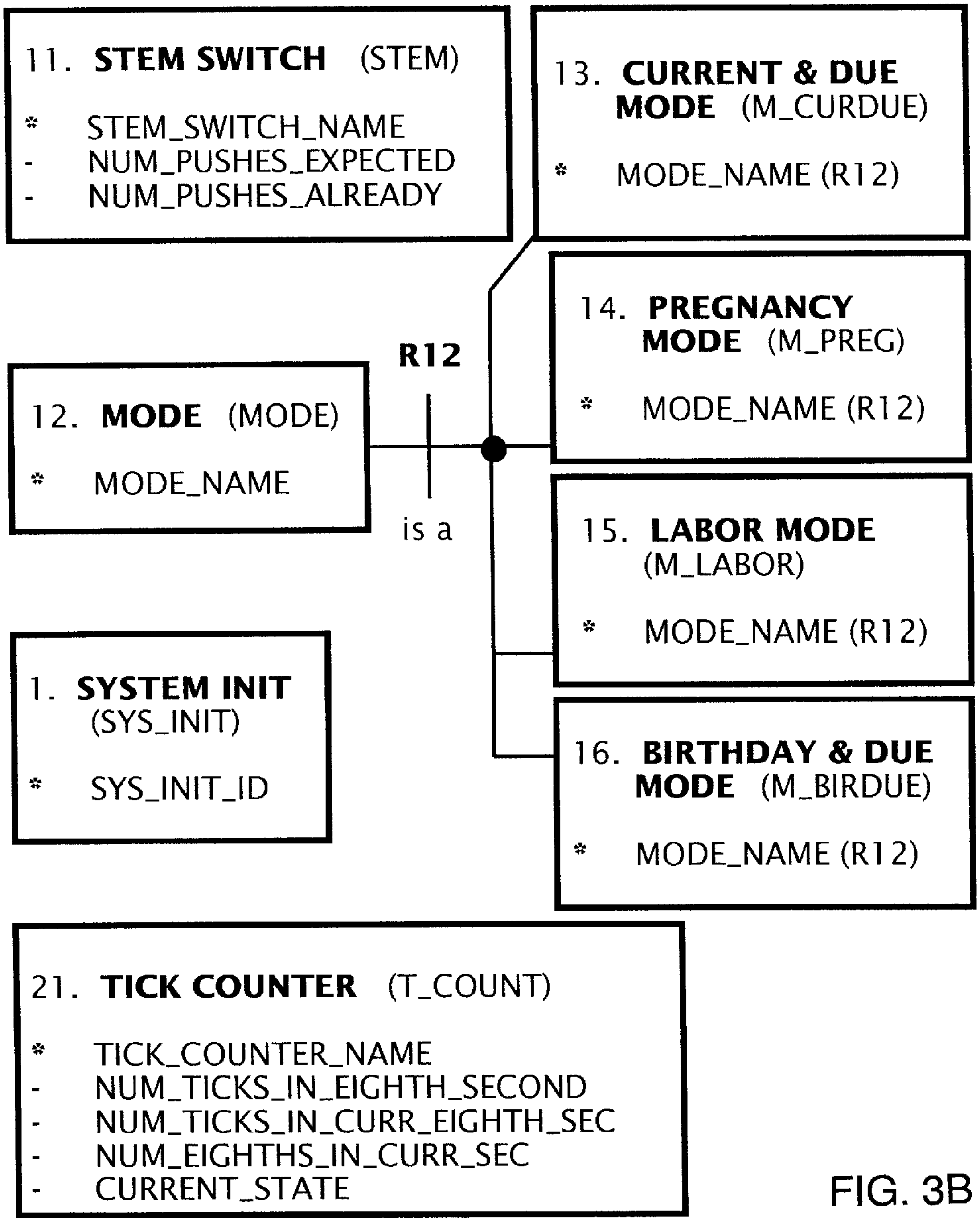
Figure 3C:
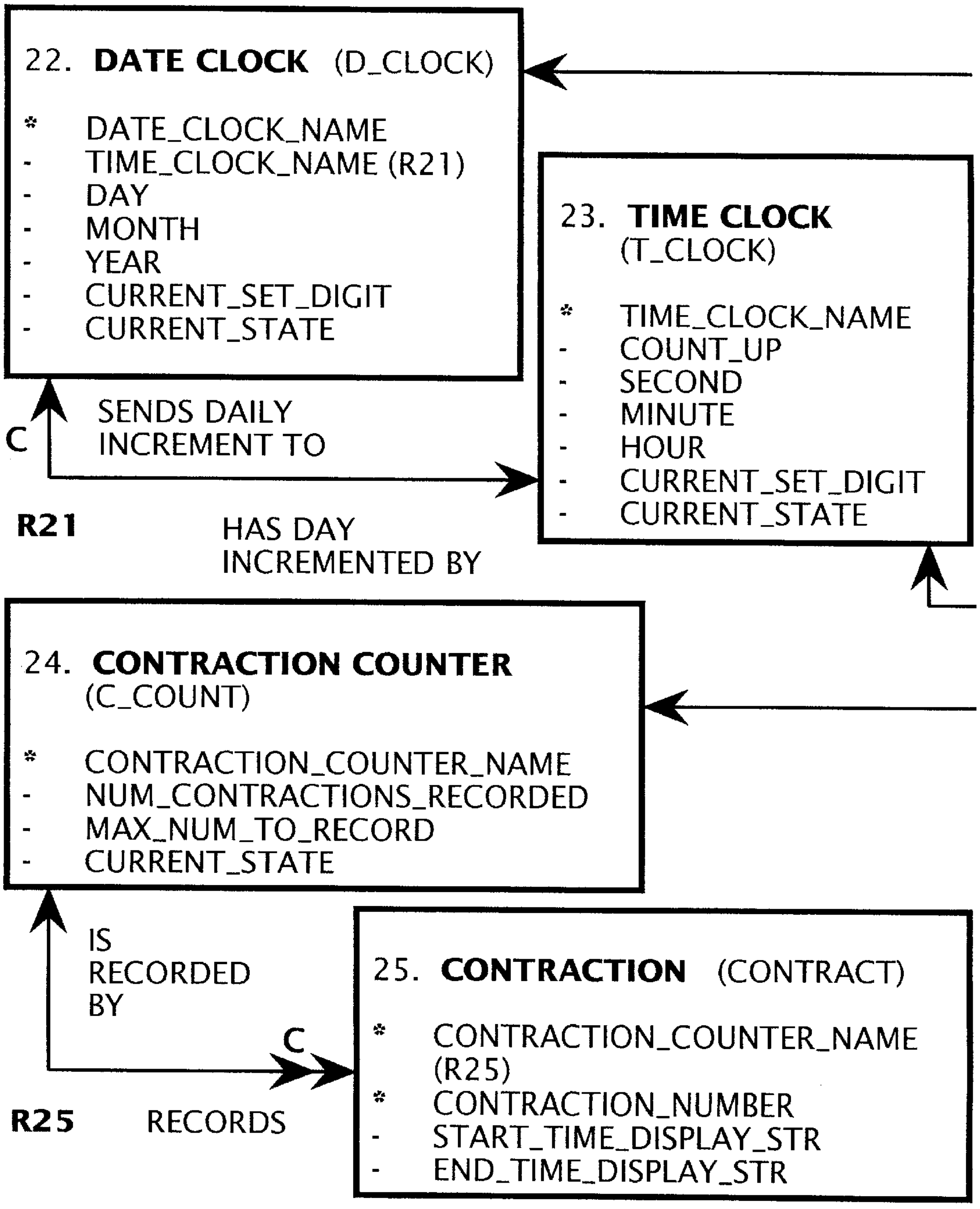
Figure 3D:
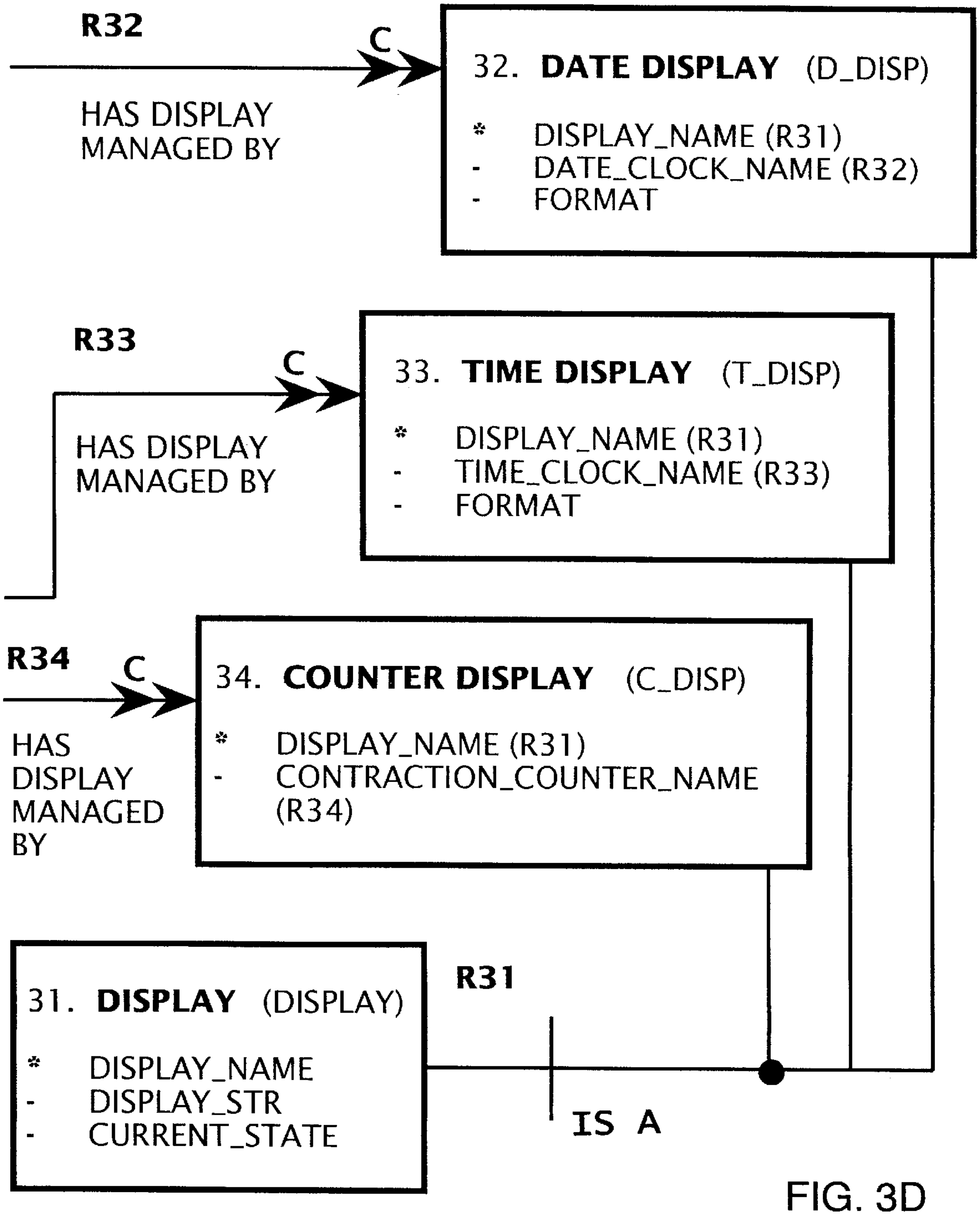

FIG. 2 is a front view of the face of the multipurpose pregnancy and labor timing device 120, showing the alpha-numeric display 140 having four readouts 152, e.g., readouts 152*a*, 152*b*, 152*c*, and 152*d*, and showing the location of the light switch 132, the mode switch 142, the set switch 144, and the increment switch 146.

Referring to FIG. 1, the multipurpose pregnancy and labor timing device 120 preferably also includes a tone generator 138. Tone generators are well-known in the art and a selected tone generator 138 is configured to emit a tone or beep each time one of the mode switch 142, set switch 144, and increment switch 146 is activated, and is configured to emit a double tone ("double beep") when the alpha-numeric display 140 changes from the first display mode to the second display mode. The tone generator 138 is also configured to produce multiple tones when the alpha-numeric display is in the fourth display mode. The multiple tones are preferably musically arranged to play a song, such as, for example, Happy Birthday.

Now the detailed operation of the preferred embodiment of the present invention 120 can be explained with reference to the computer program appendix (the "action specification logic") and to FIGS. 3A through 17.

The internal control logic of the multipurpose pregnancy and labor timing device 120 has been modeled using the graphical modeling techniques of the well-known Shlaer-Mellor Object Oriented Analysis Method. This method has been selected for capture of the control logic because it (a) supports interaction with pre-existing and well-known building blocks, (b) supports natural partitioning of internal control logic, (c) supports formal and detailed capture of internal control logic in an implementation-independent manner, and (d) supports execution of the internal control logic in order to simulate and verify the operation of the device 120.

Explanation of the Shlaer-Mellor Object-Oriented Analysis Method can be found in the following books: Sally Shlaer and Stephen J. Mellor, *Object Oriented Systems Analysis: Modeling the World in Data*, Prentice Hall, Englewood Cliffs, N.J., 1988; and Sally Shlaer and Stephen J. Mellor, *Object Lifecycles: Modeling the World in States*, Prentice Hall, Englewood Cliffs, N.J., 1992.

Figure 4A:
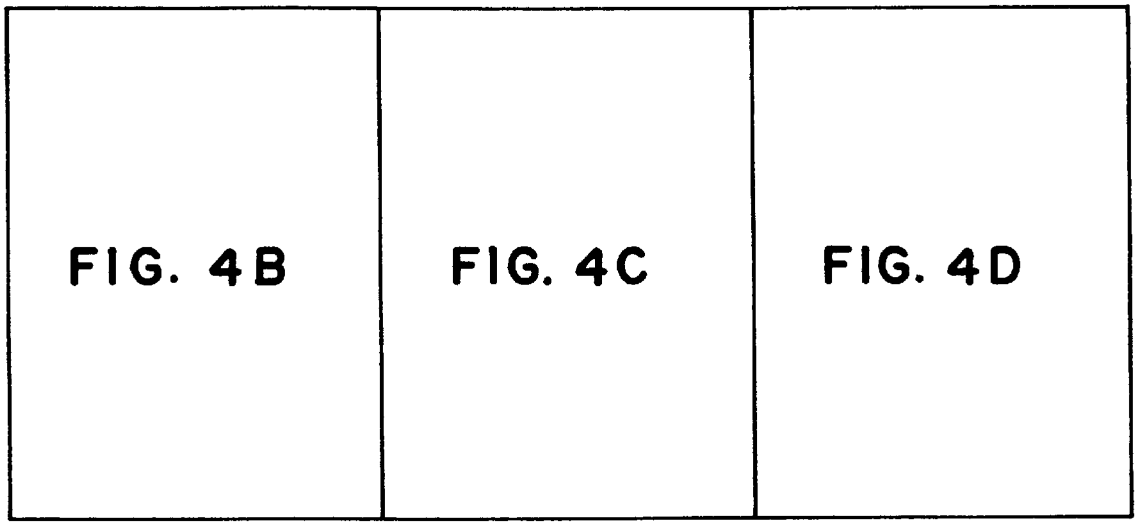
FIG. 4A shows the organization of FIGS. 4B, 4C, and 4D, which together represent, as an object communication model, a flow diagram showing a preferred operation of the present invention.
Figure 4B:
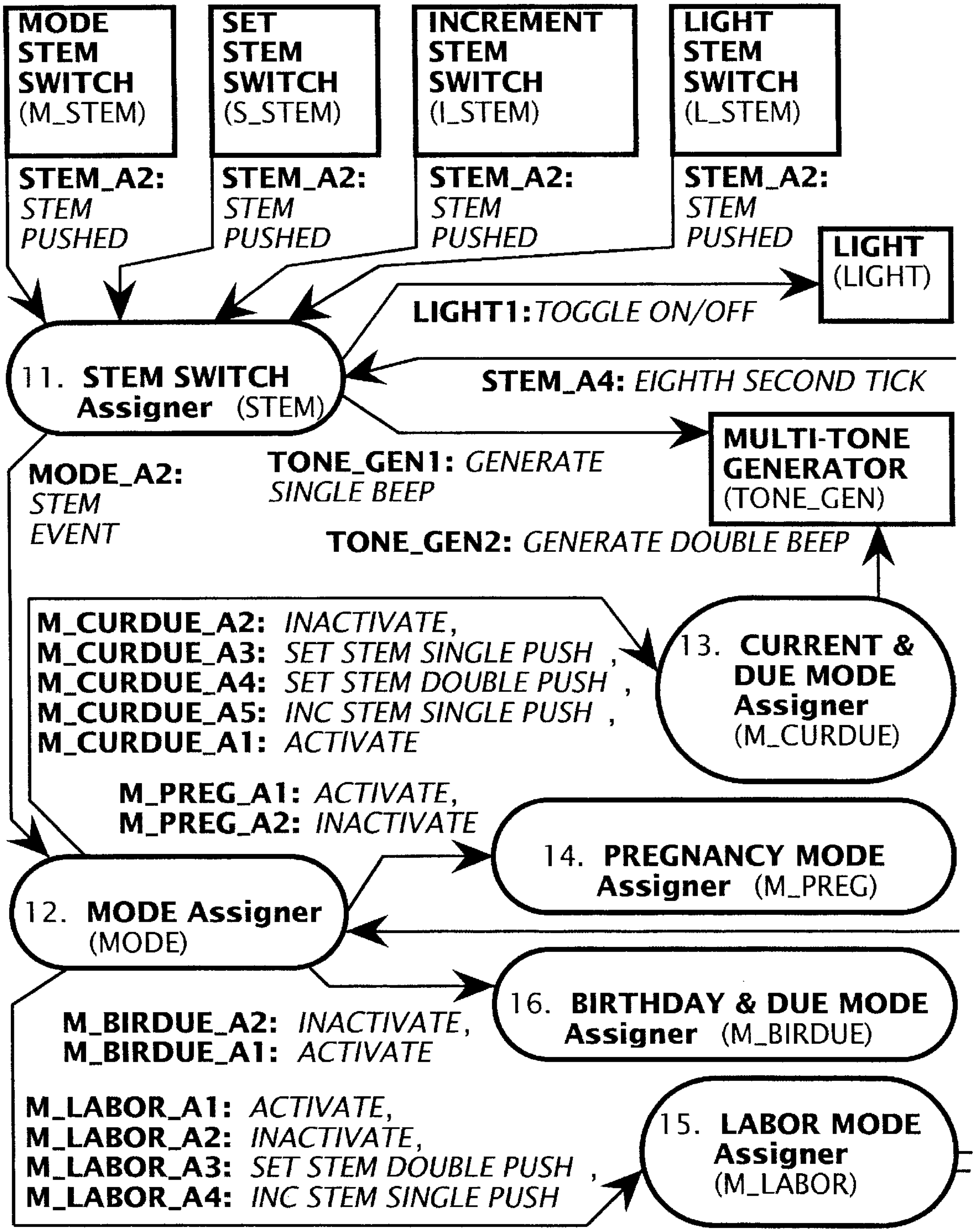
Figure 4C:
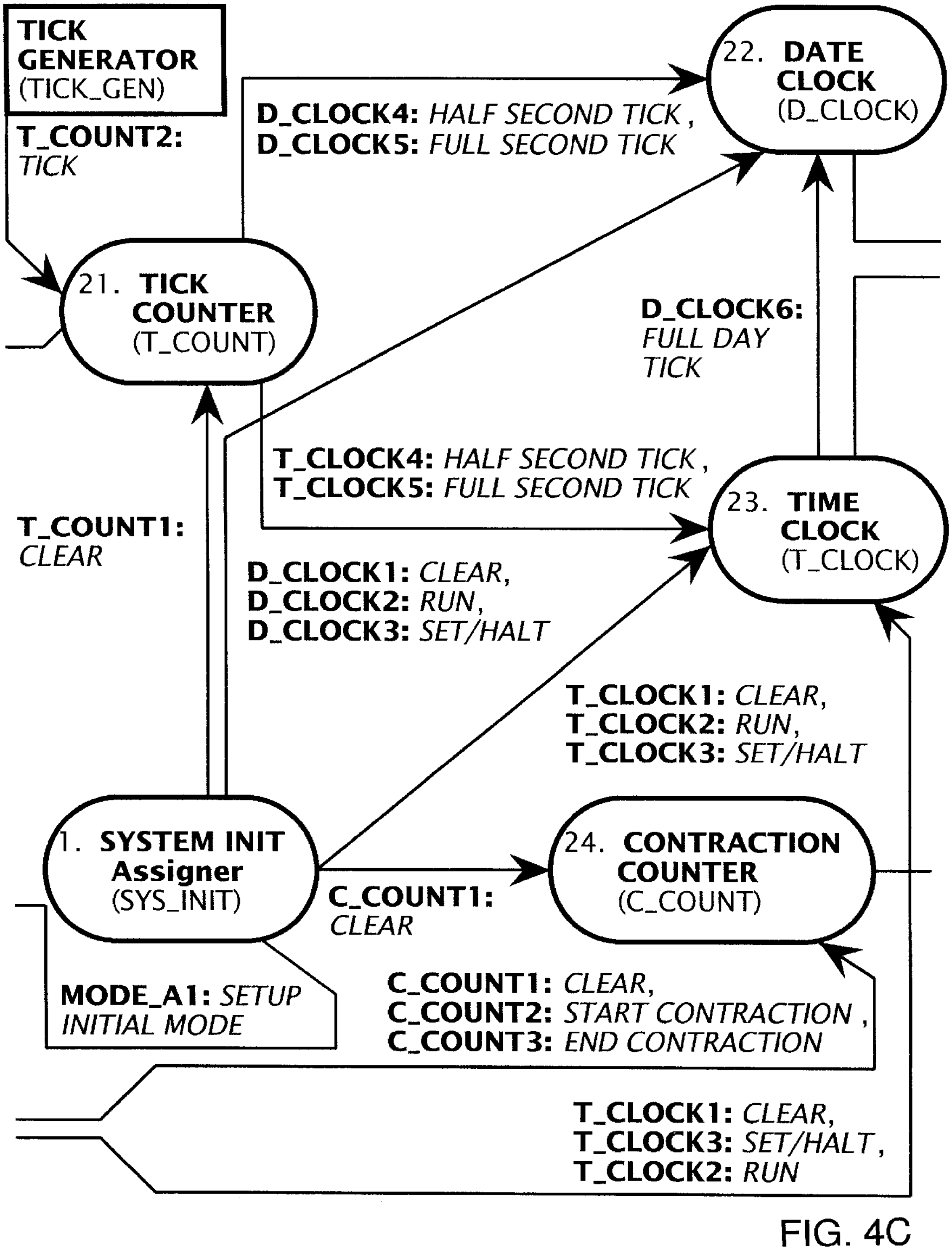
Figure 4D:
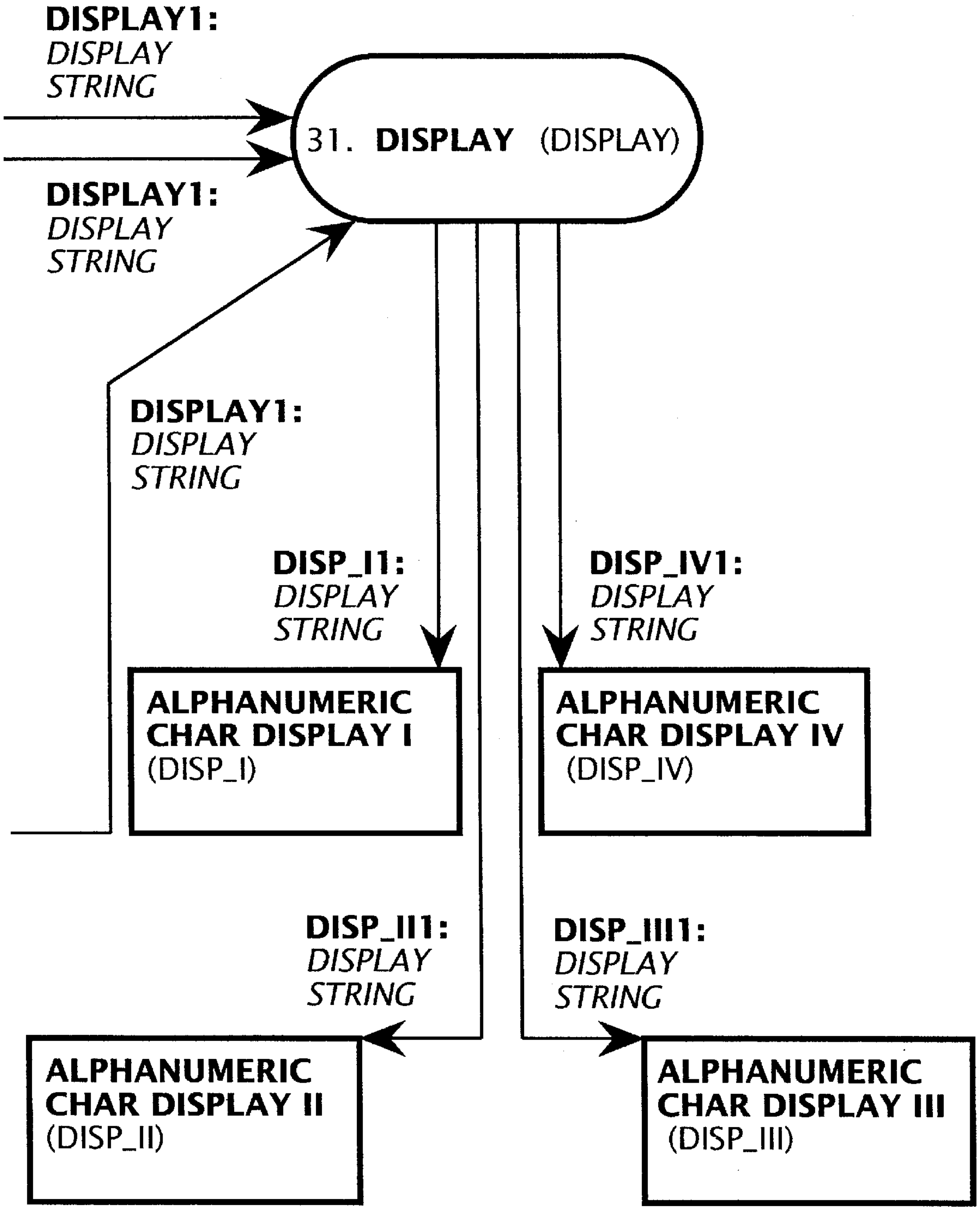
Figure 5:
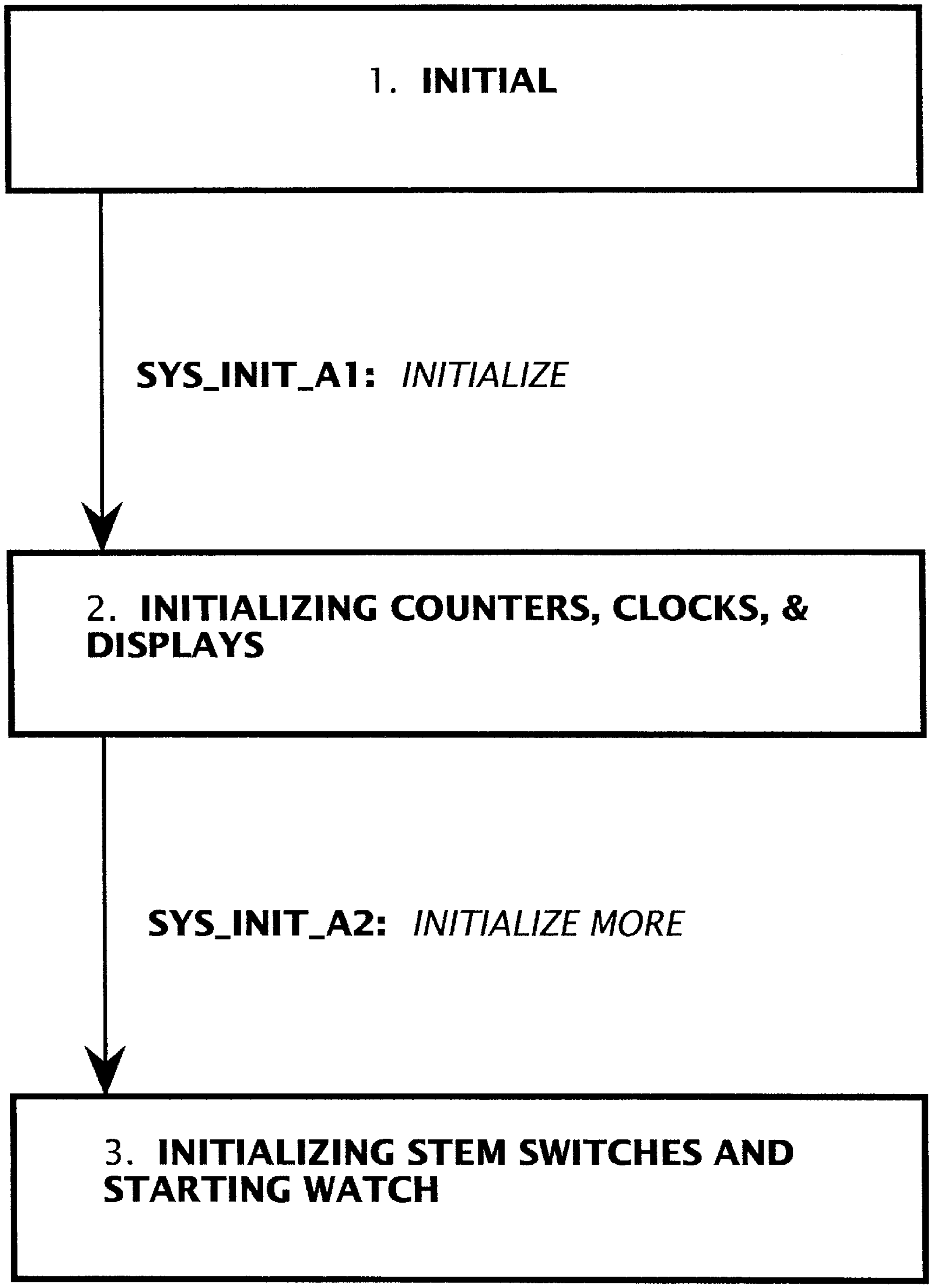
FIG. 5 shows the state model for the "SYSTEM INIT" assigner block (1) of FIG. 3B.
Figure 6:
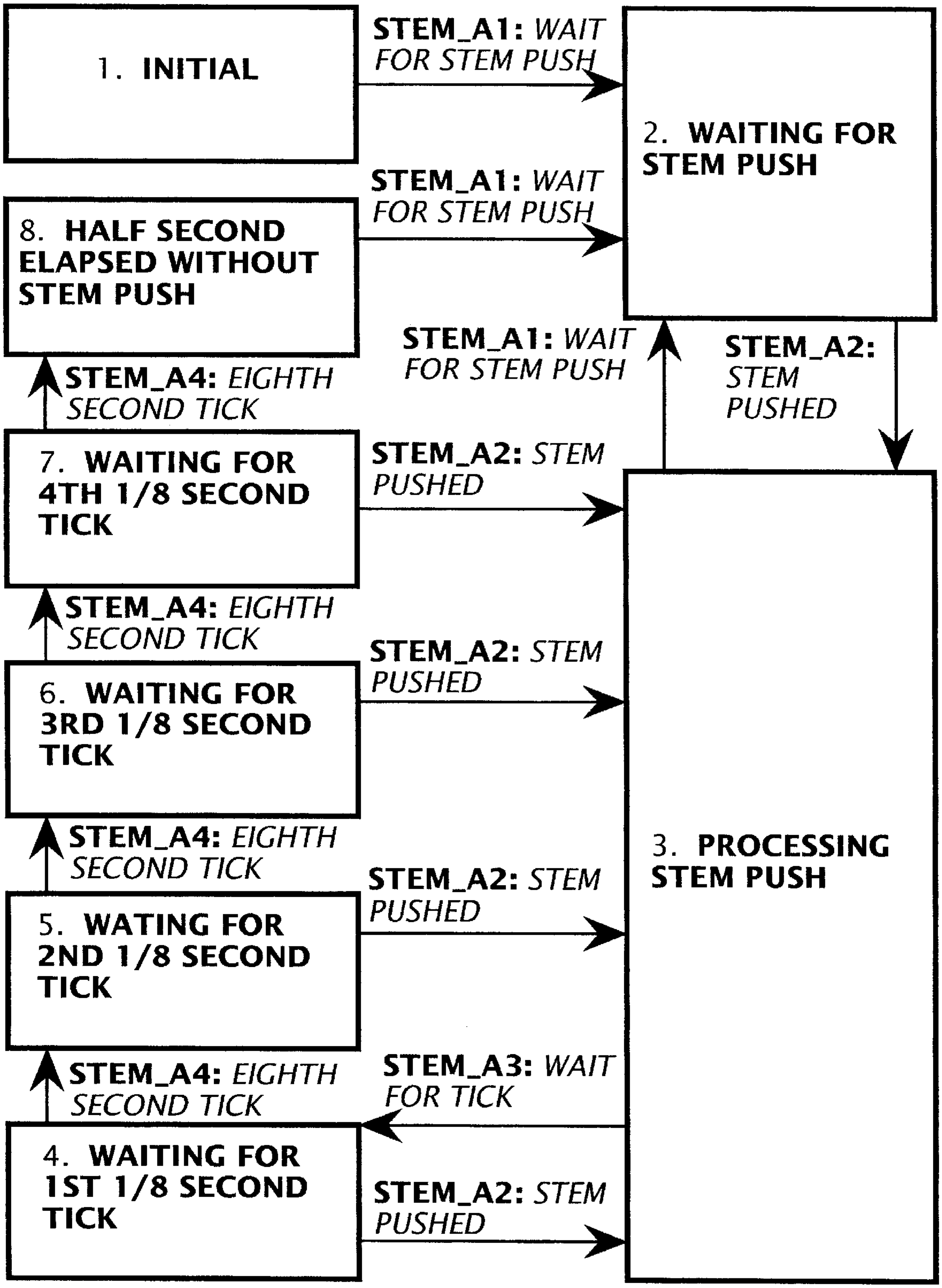
FIG. 6 shows the state model for the "STEM SWITCH" assigner block (11) of FIG. 3B.
Figure 7:
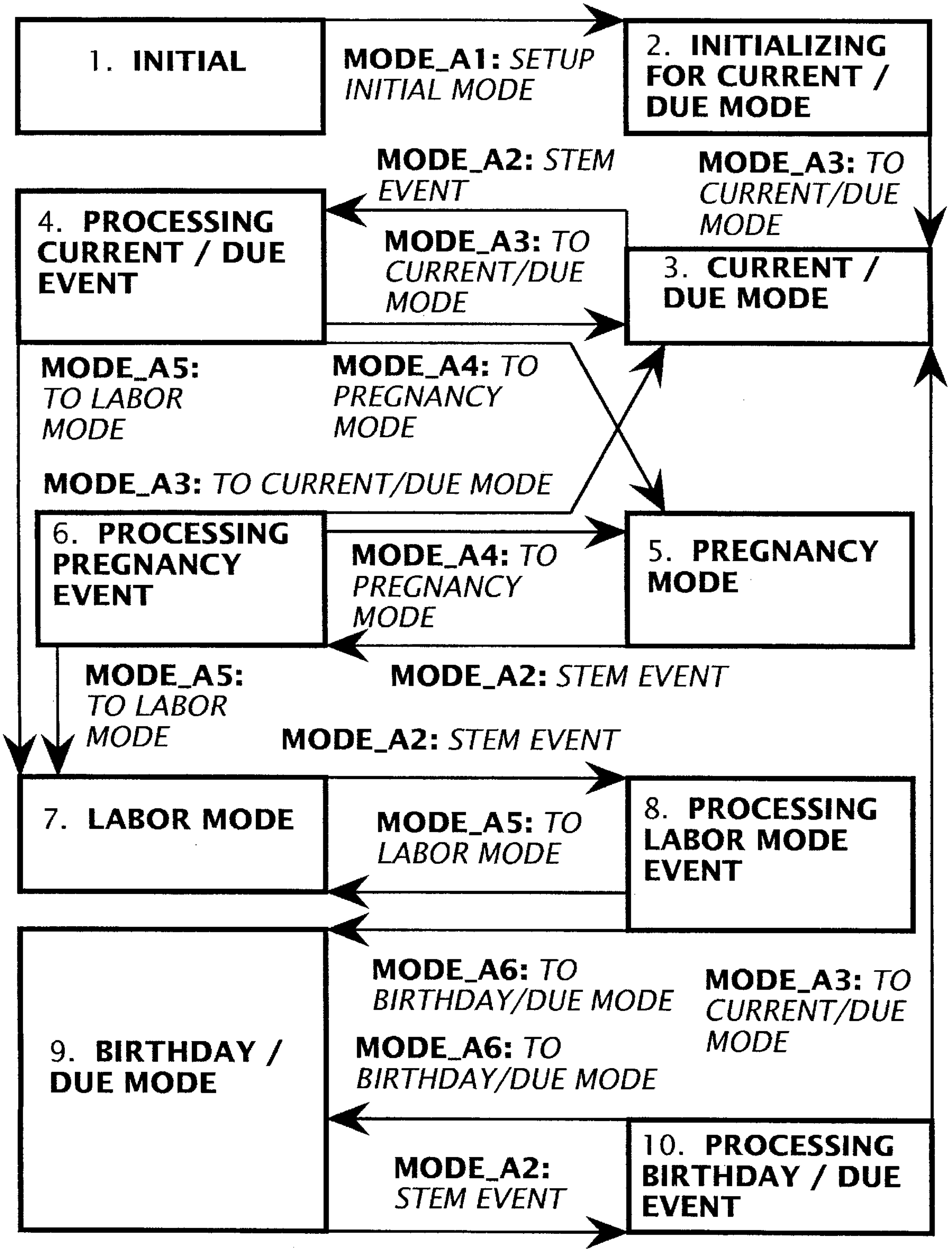
FIG. 7 shows the state model for the "MODE" assigner block (12) of FIG. 3B.
Figure 8A:
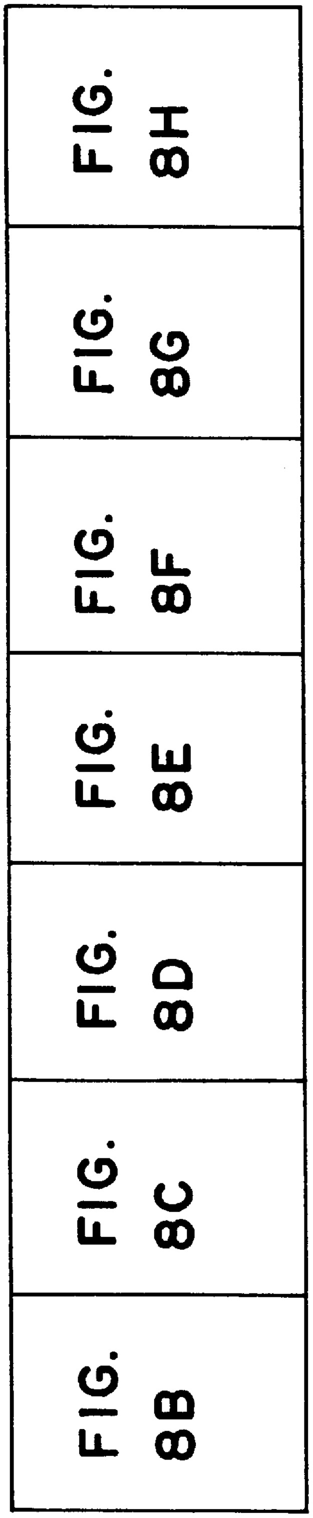
FIG. 8A shows the organization of FIGS. 8B, 8C, 8D, 8E, 8F, 8G, and 8H, which together represent the state model for the "CURRENT & DUE MODE" assigner block (13) of FIG. 3B.
Figure 8B:
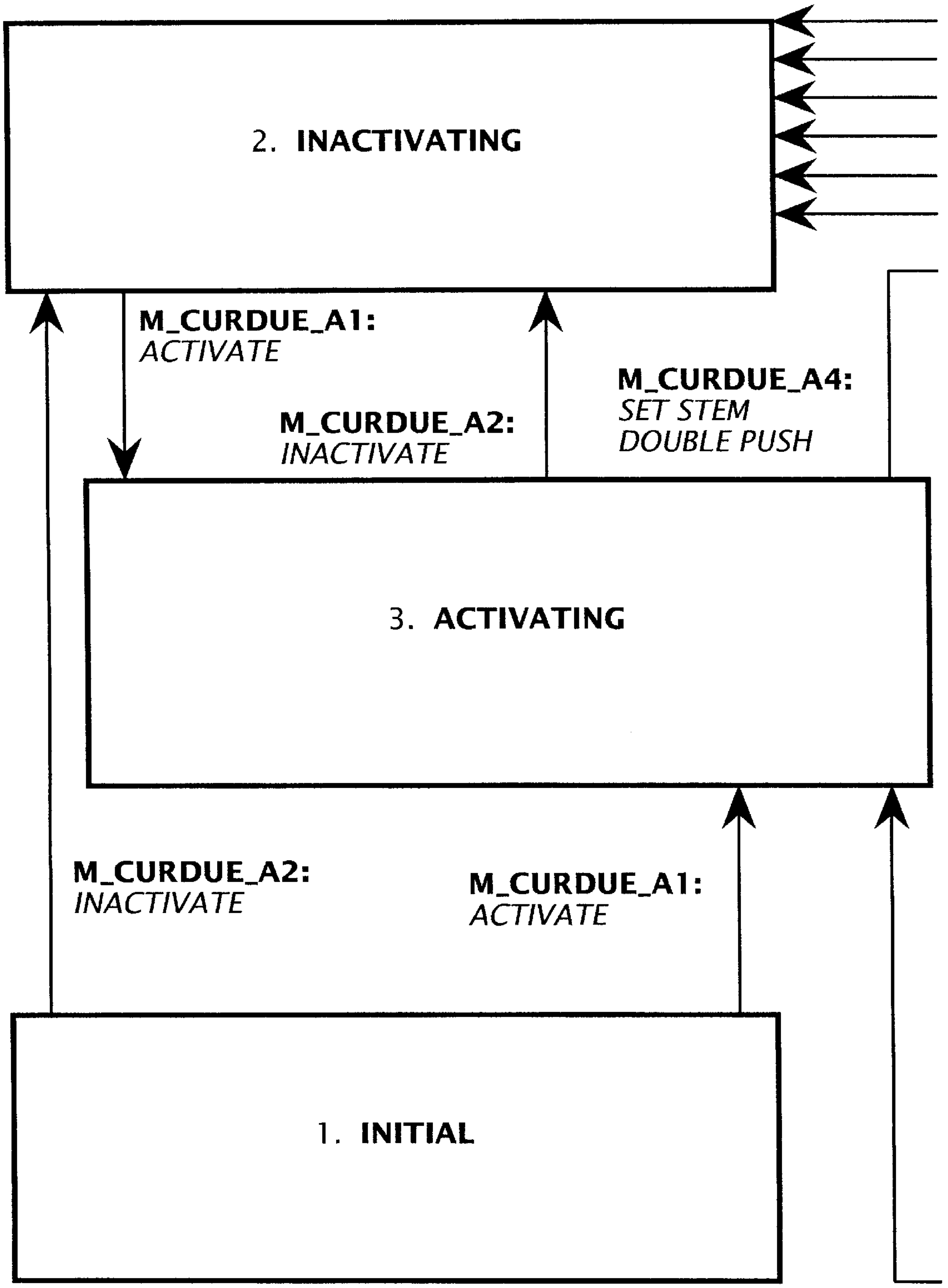
Figure 8C:
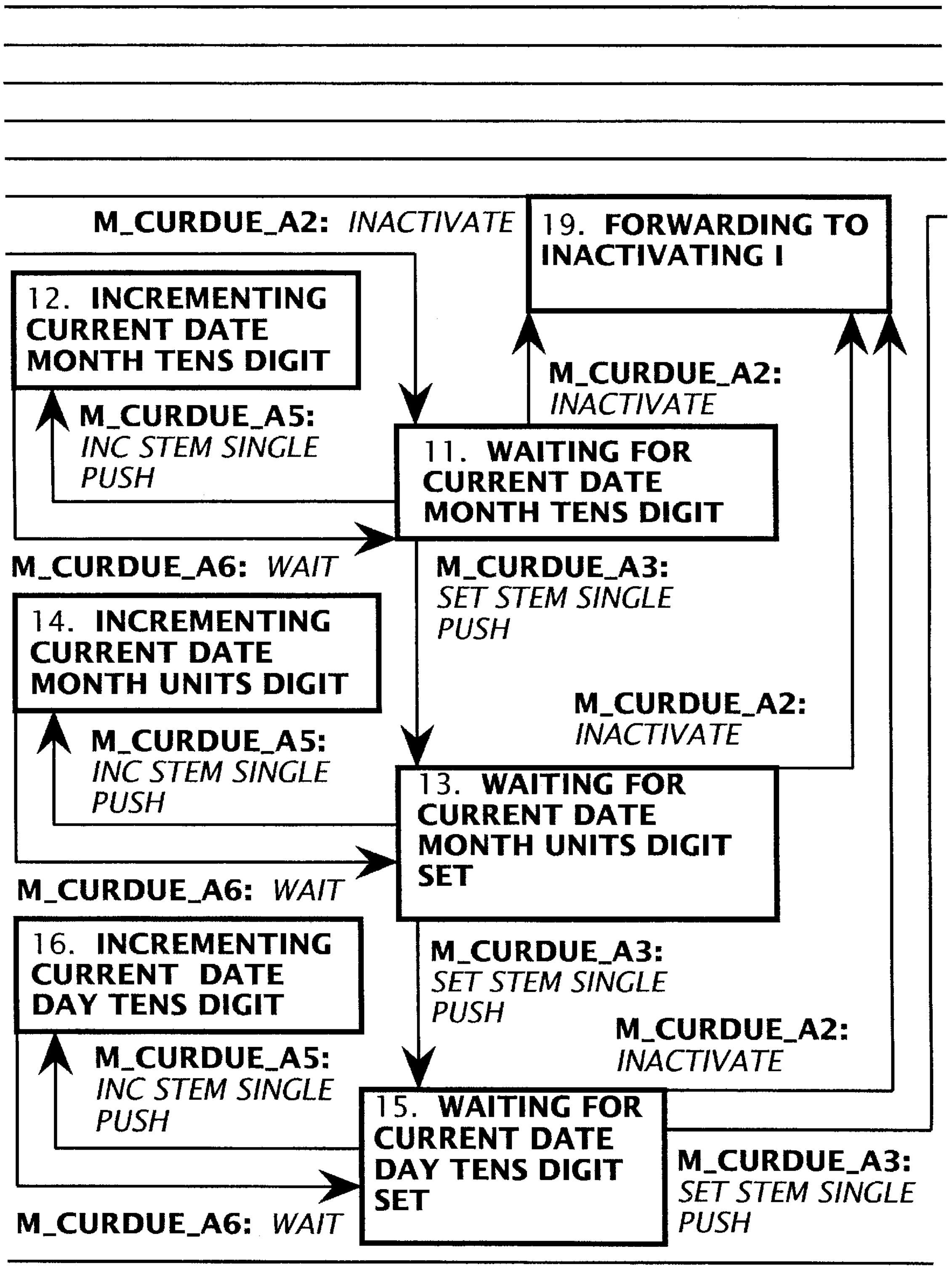
Figure 8D:
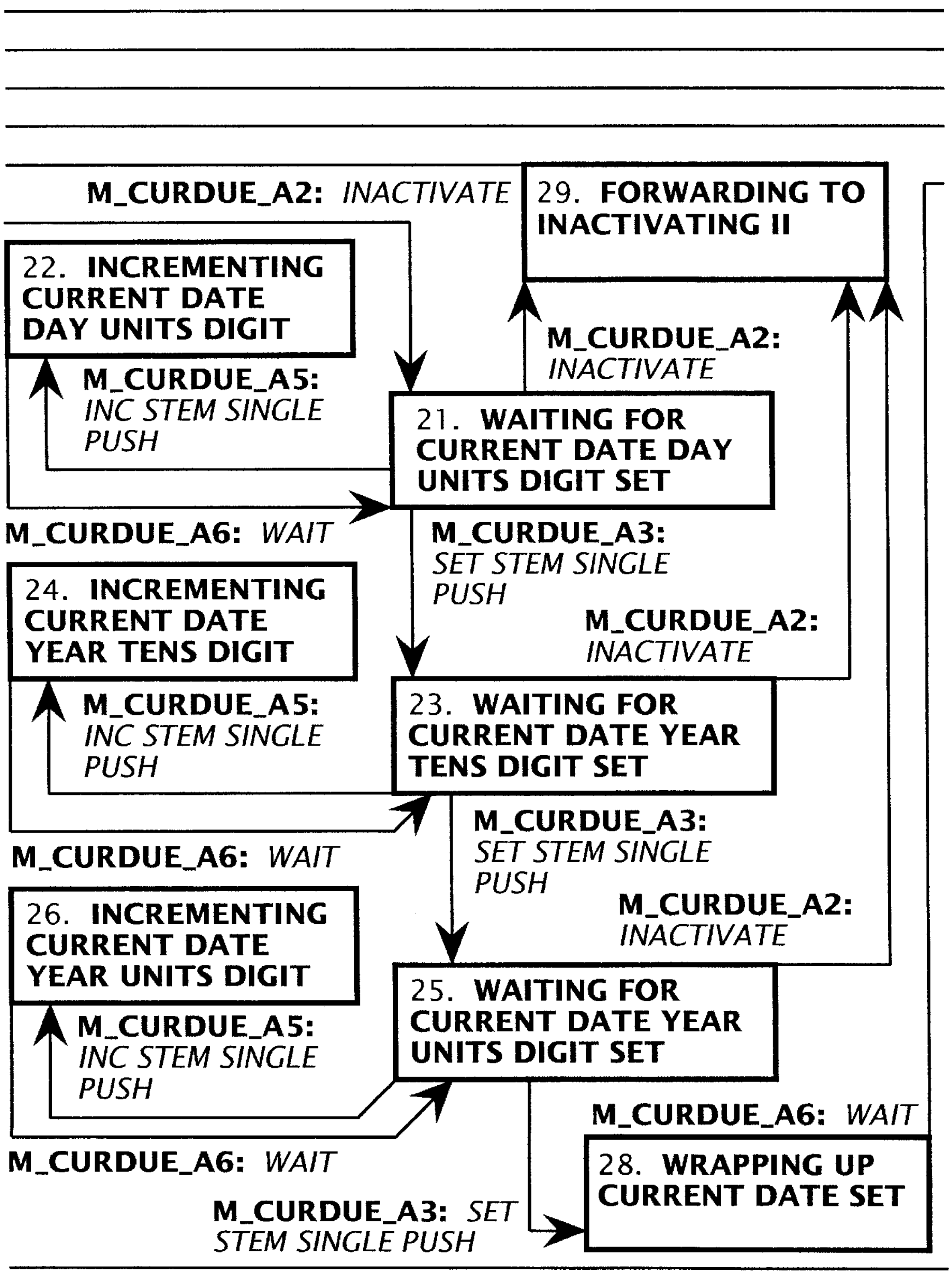
Figure 8E:
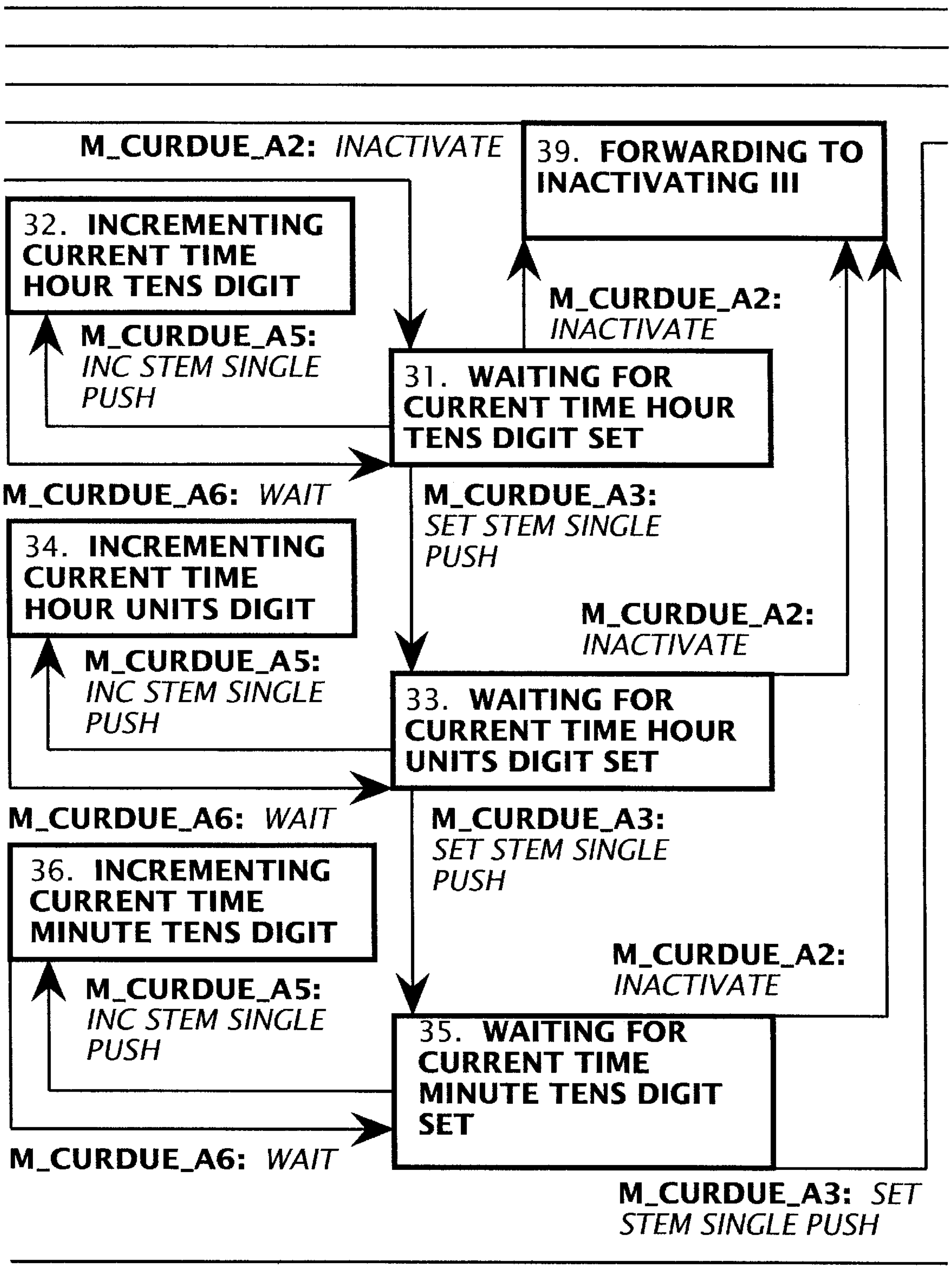
Figure 8F:
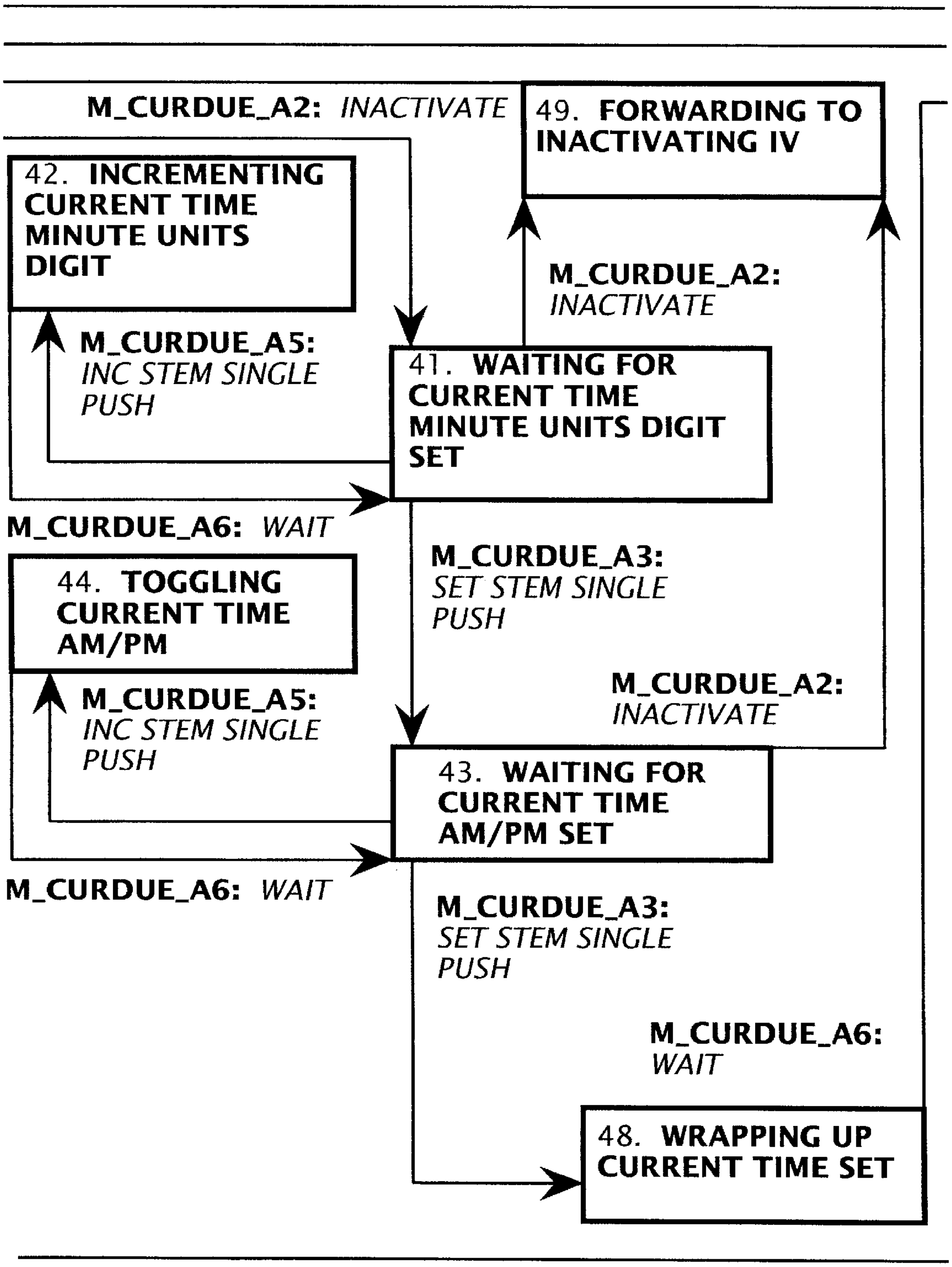
Figure 8G:
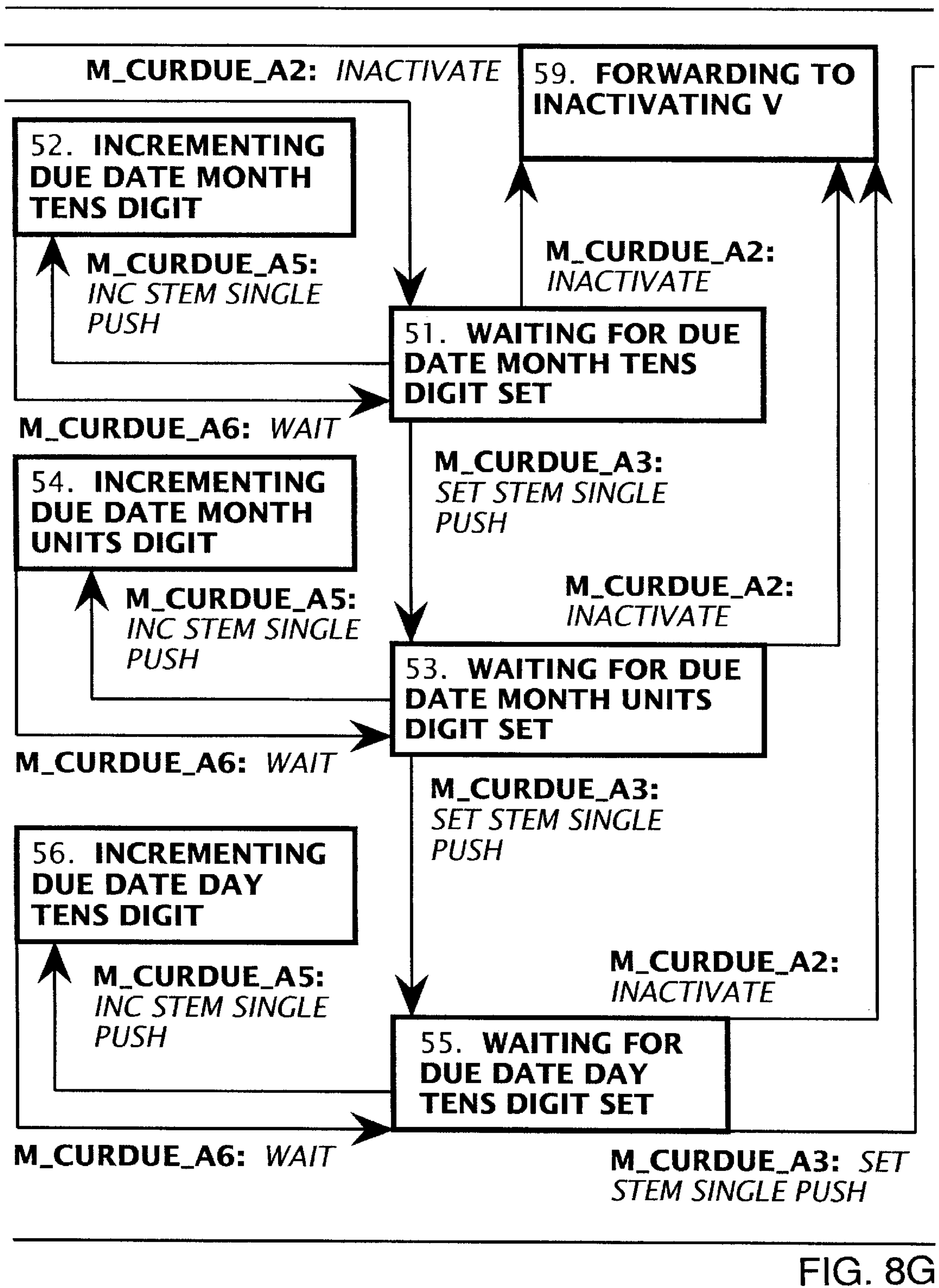
Figure 8H:
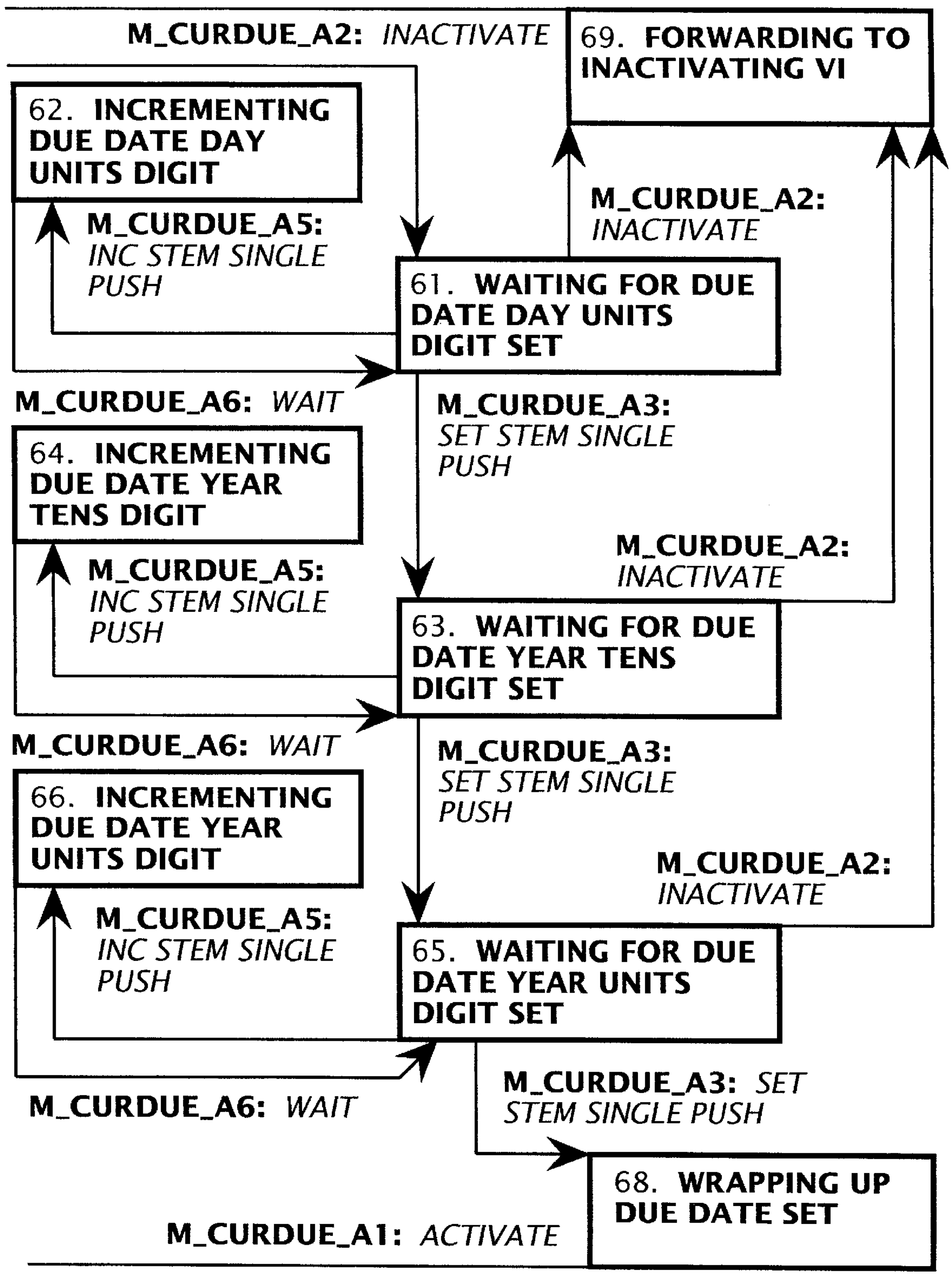
Figure 9:
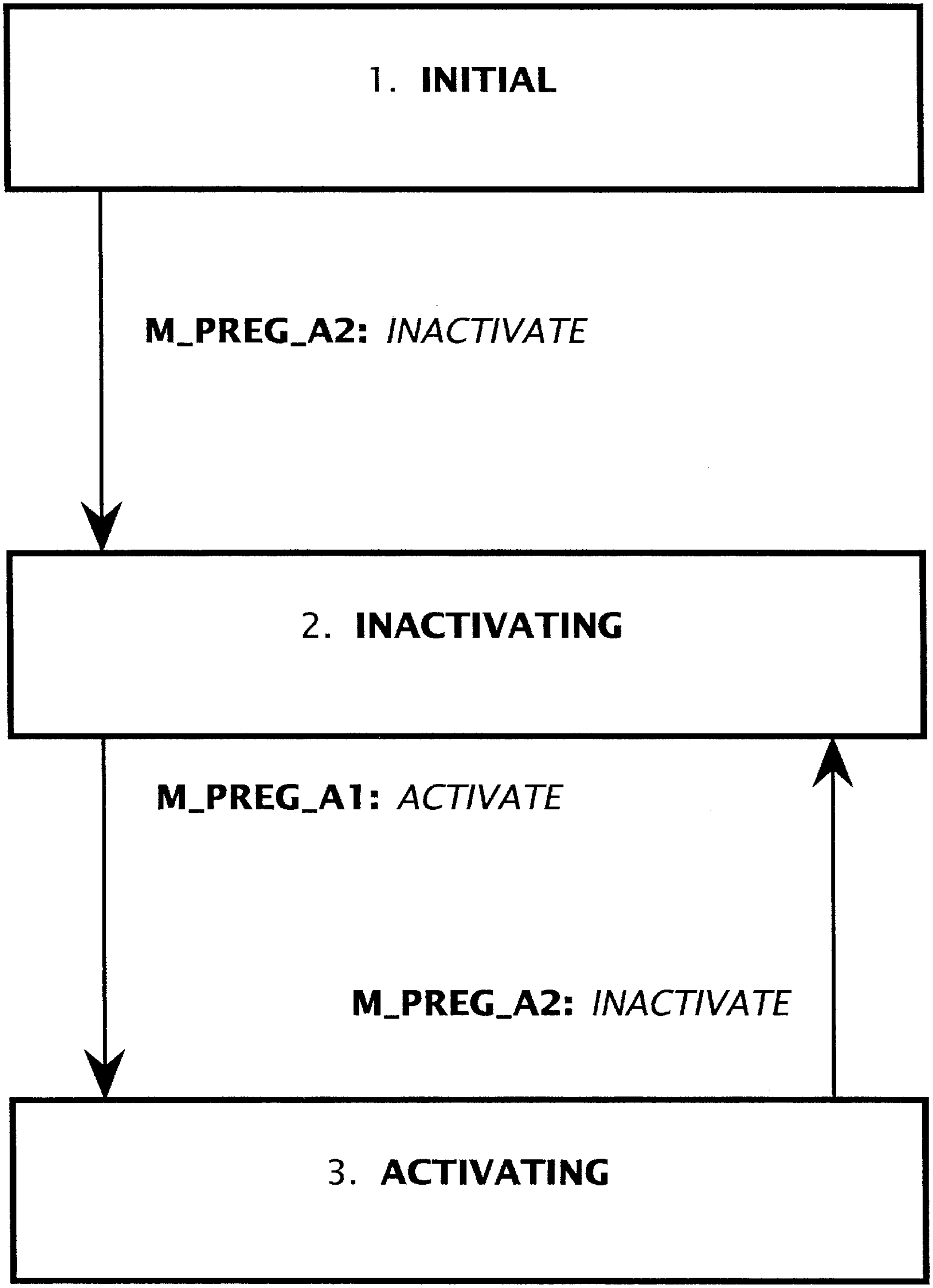
FIG. 9 shows the state model for the "PREGNANCY MODE" assigner block (14) of FIG. 3B.
Figure 10:
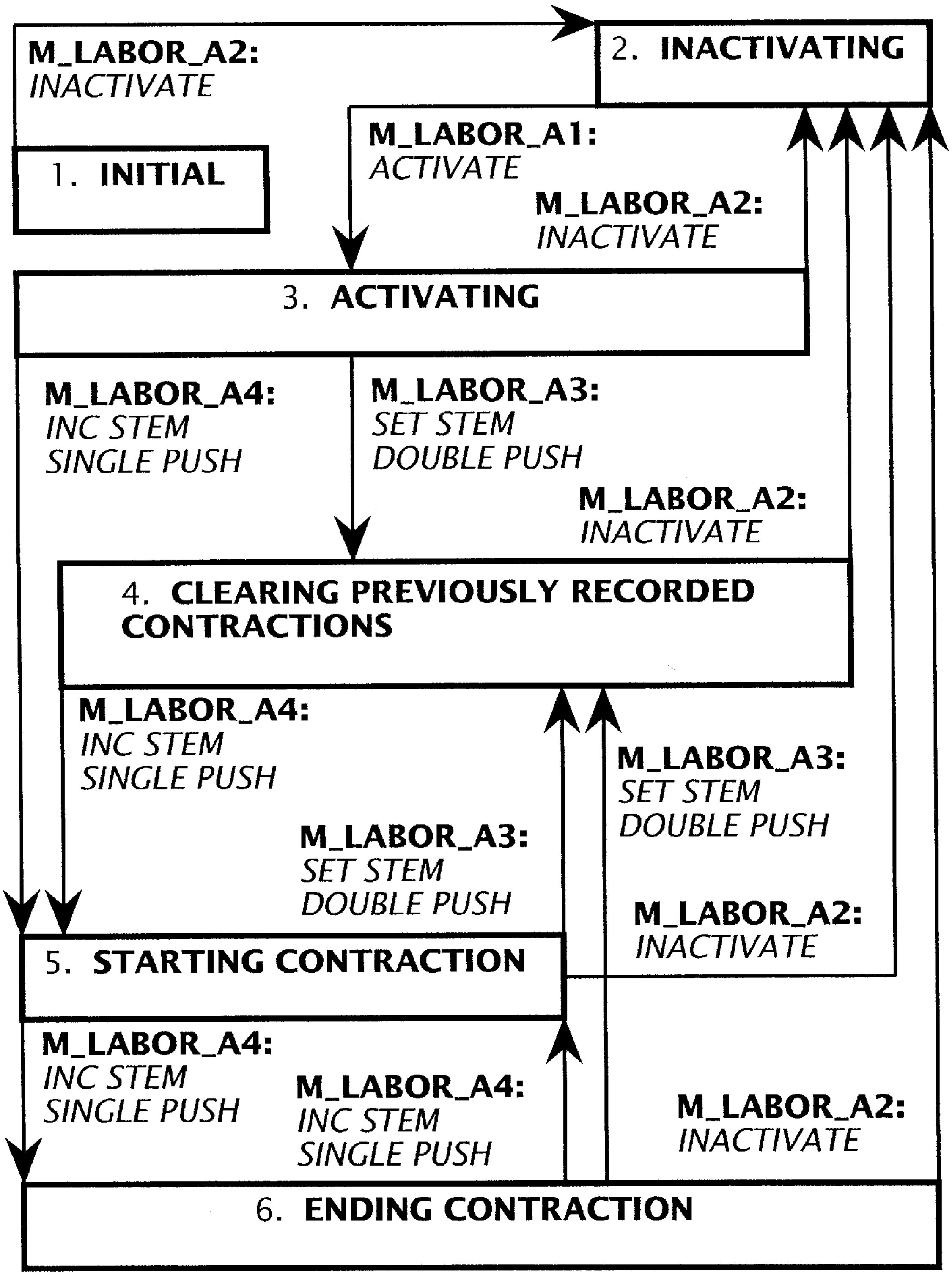
FIG. 10 shows the state model for the "LABOR MODE" assigner block (15) of FIG. 3B.
Figure 11:
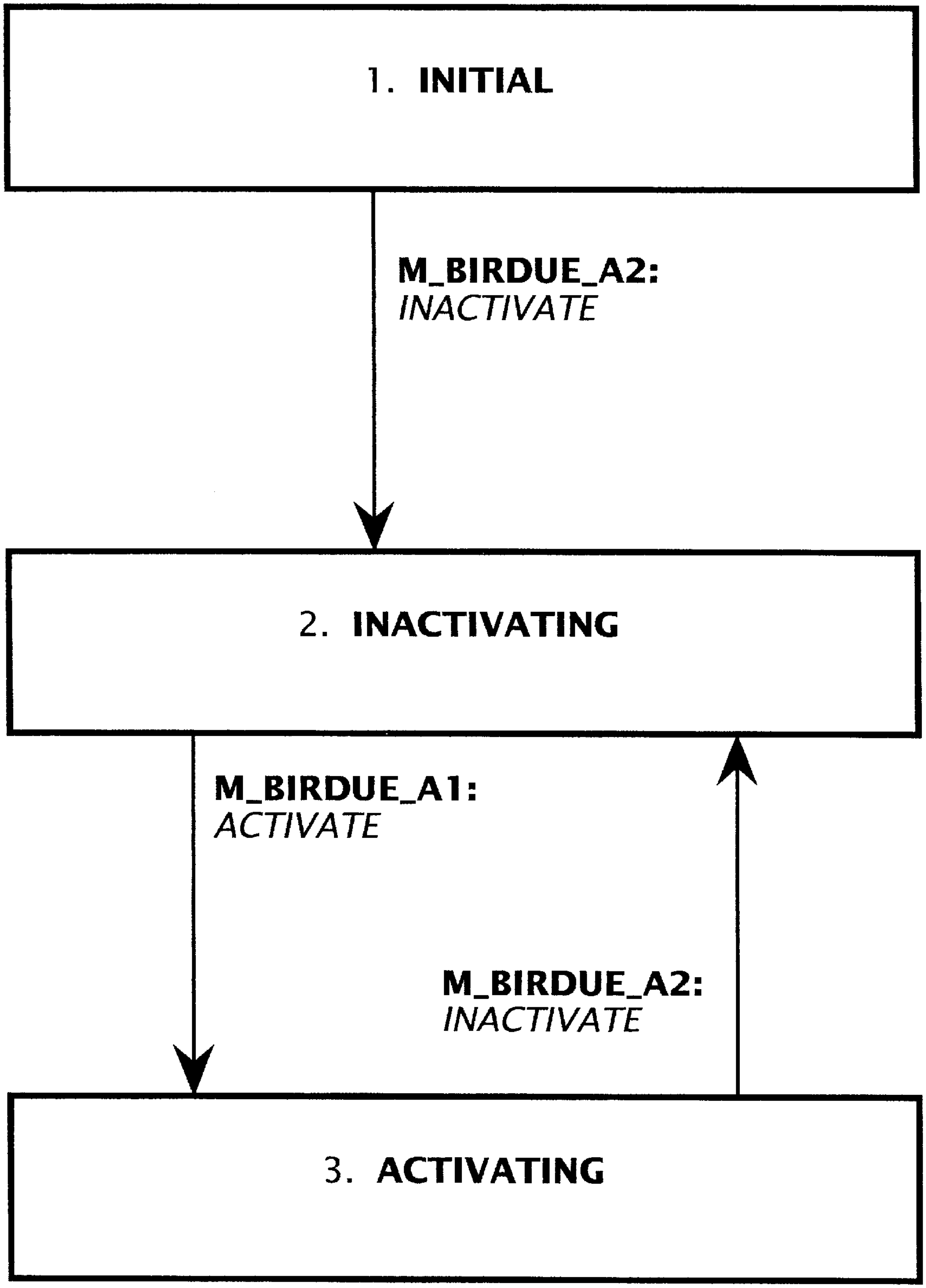
FIG. 11 shows the state model for the "BIRTHDAY & DUE MODE" assigner block (16) of FIG. 3B.
Figure 12:
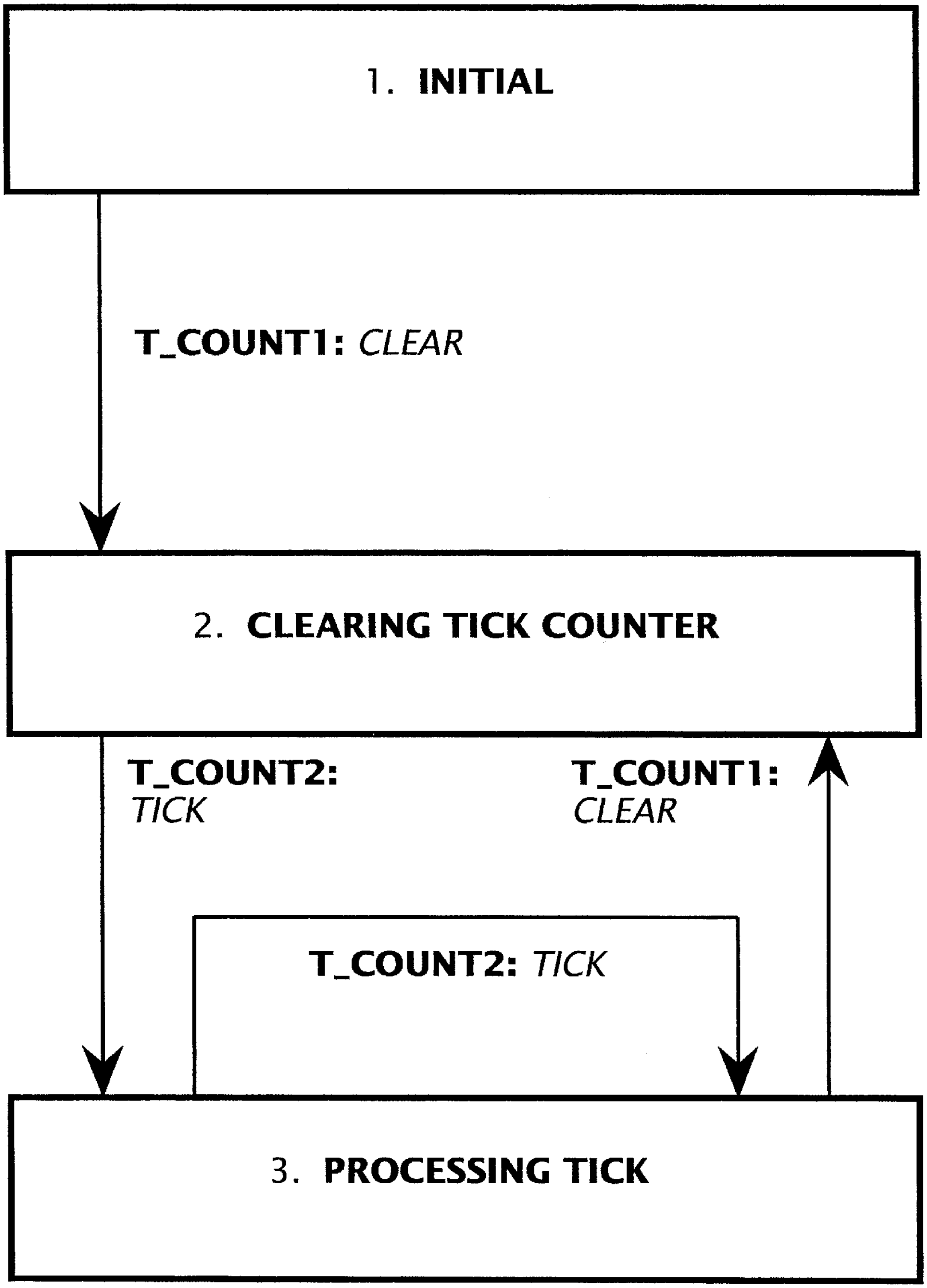
FIG. 12 shows the state model for the "TICK COUNTER" assigner block (21) of FIG. 3B.
Figure 13:
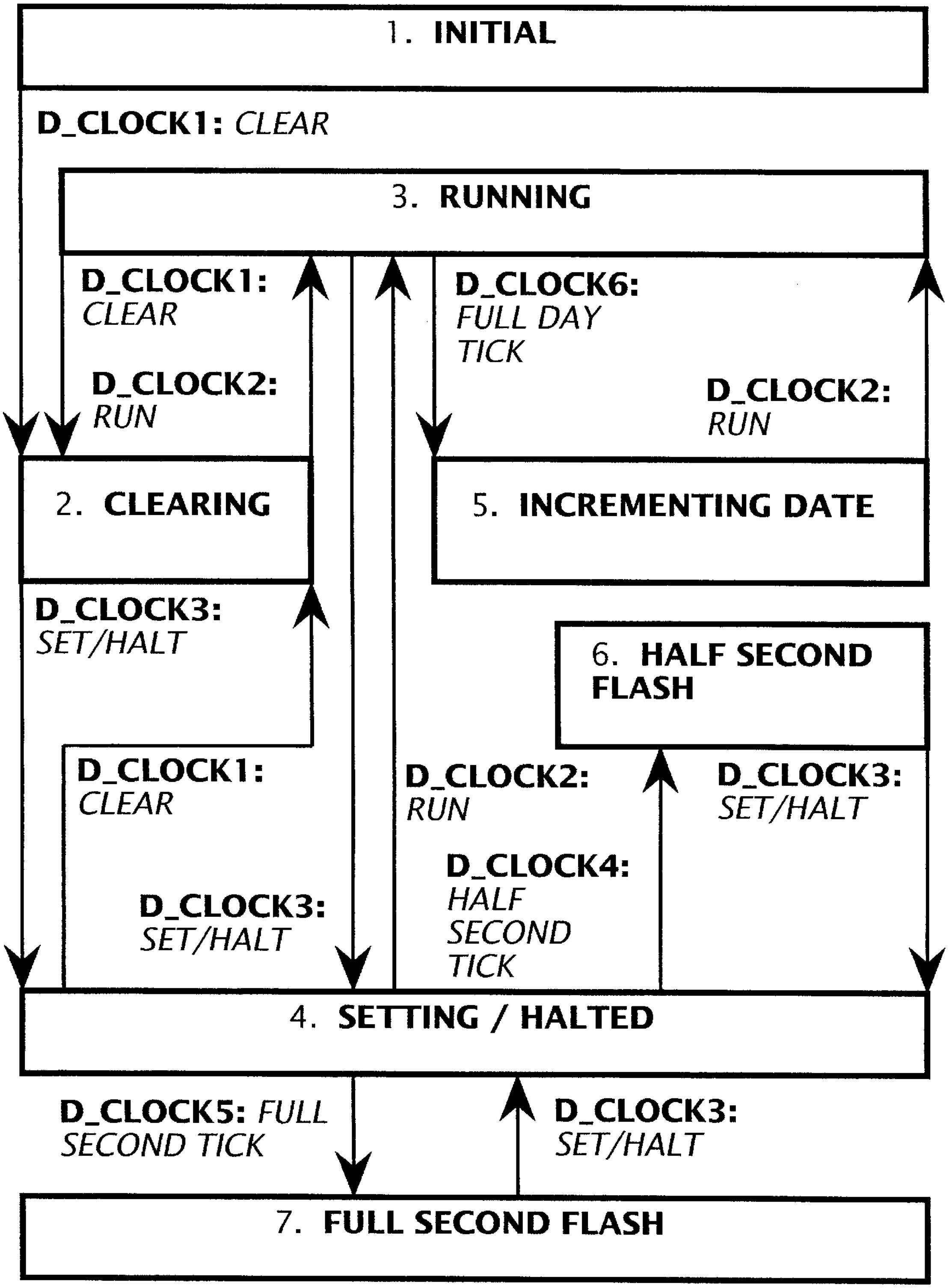
FIG. 13 shows the state model for the "DATE CLOCK" assigner block (22) of FIG. 3C.
Figure 14:
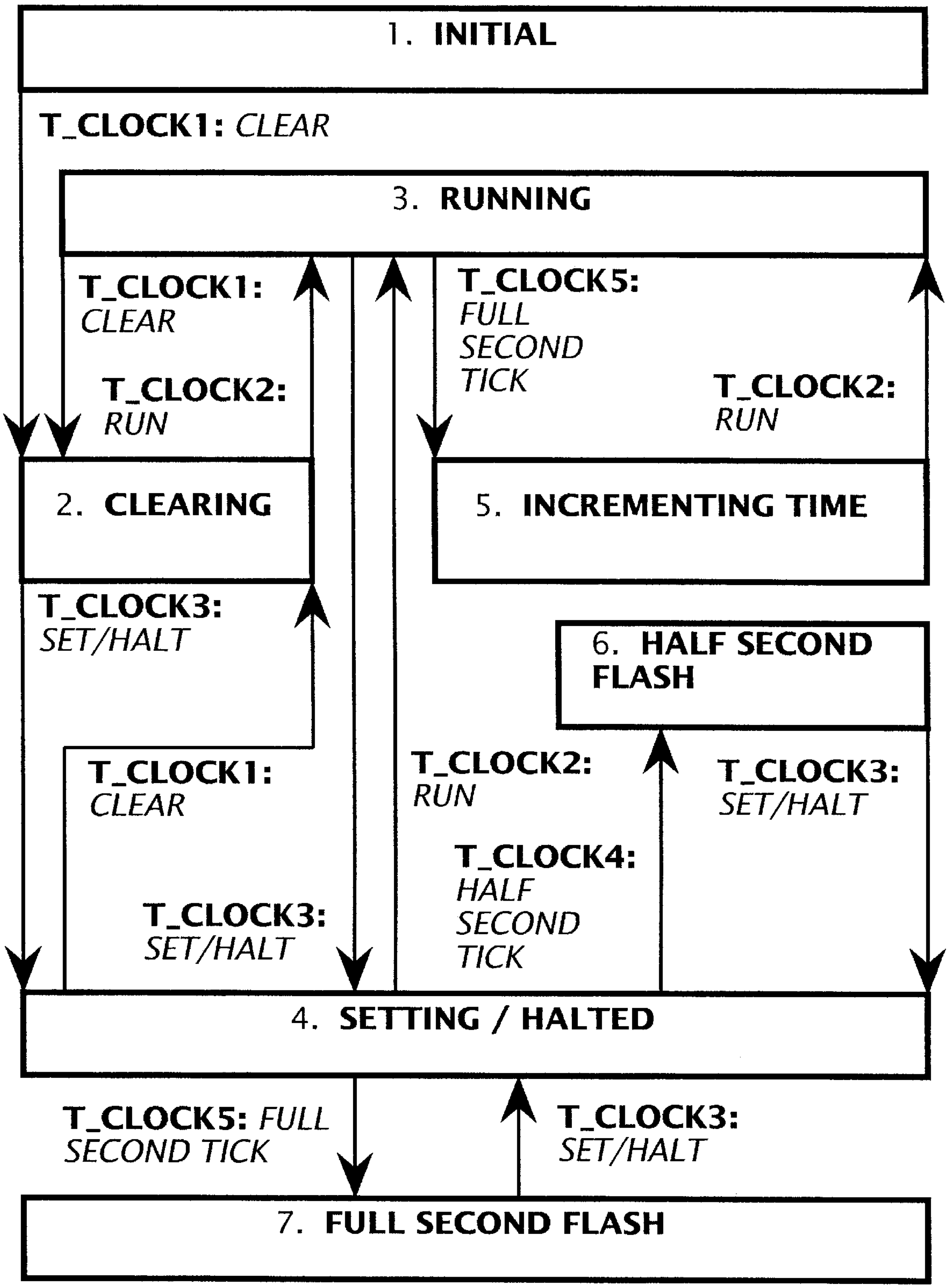
FIG. 14 shows the state model for the "TIME CLOCK" assigner block (23) of FIG. 3C.
Figure 15:
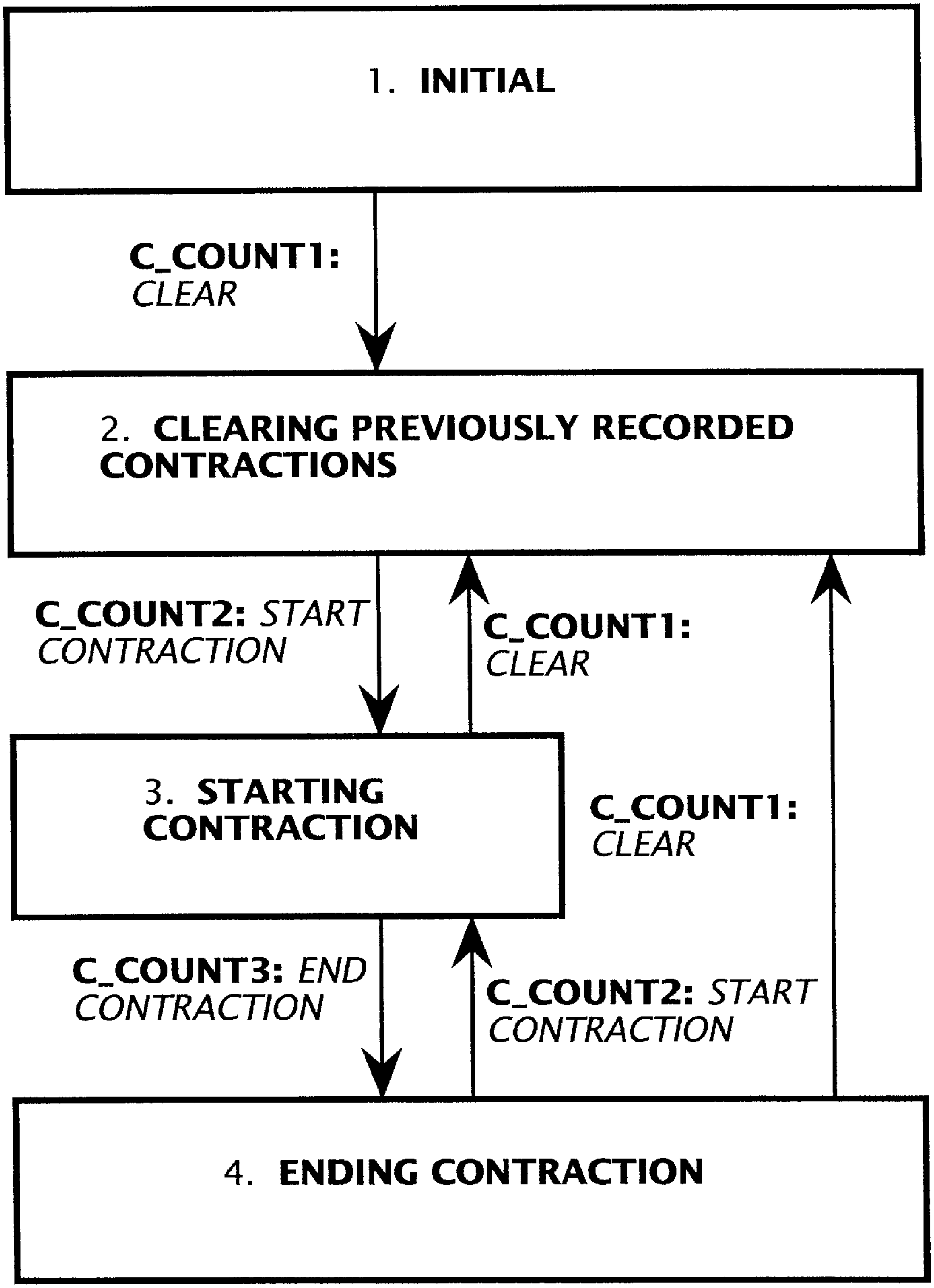
FIG. 15 shows the state model for the "CONTRACTION COUNTER" assigner block (24) of FIG. 3C.
Figure 16:
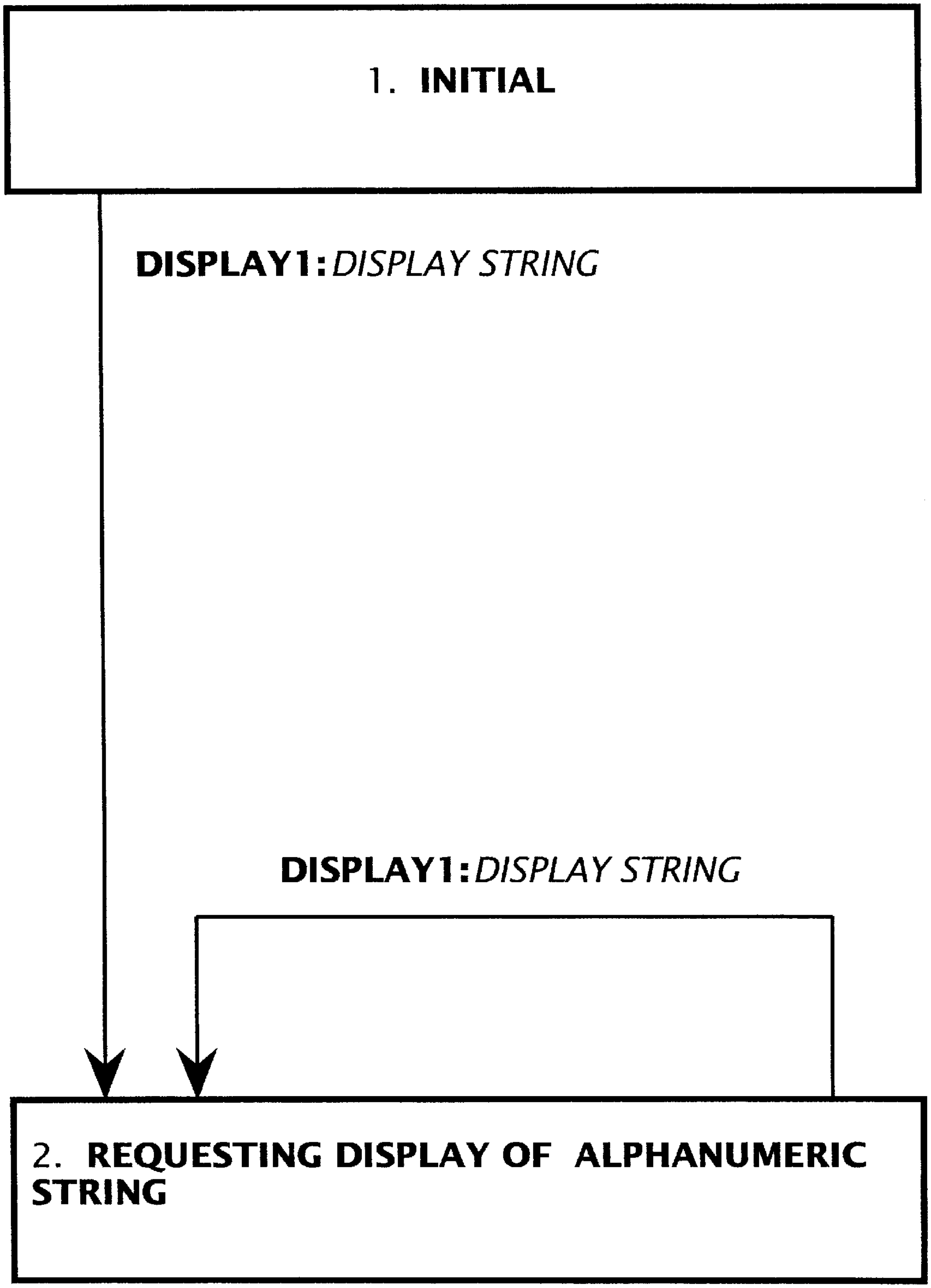
FIG. 16 shows the state model for the "DISPLAY" assigner block (31) of FIG. 3D.
Figure 17:
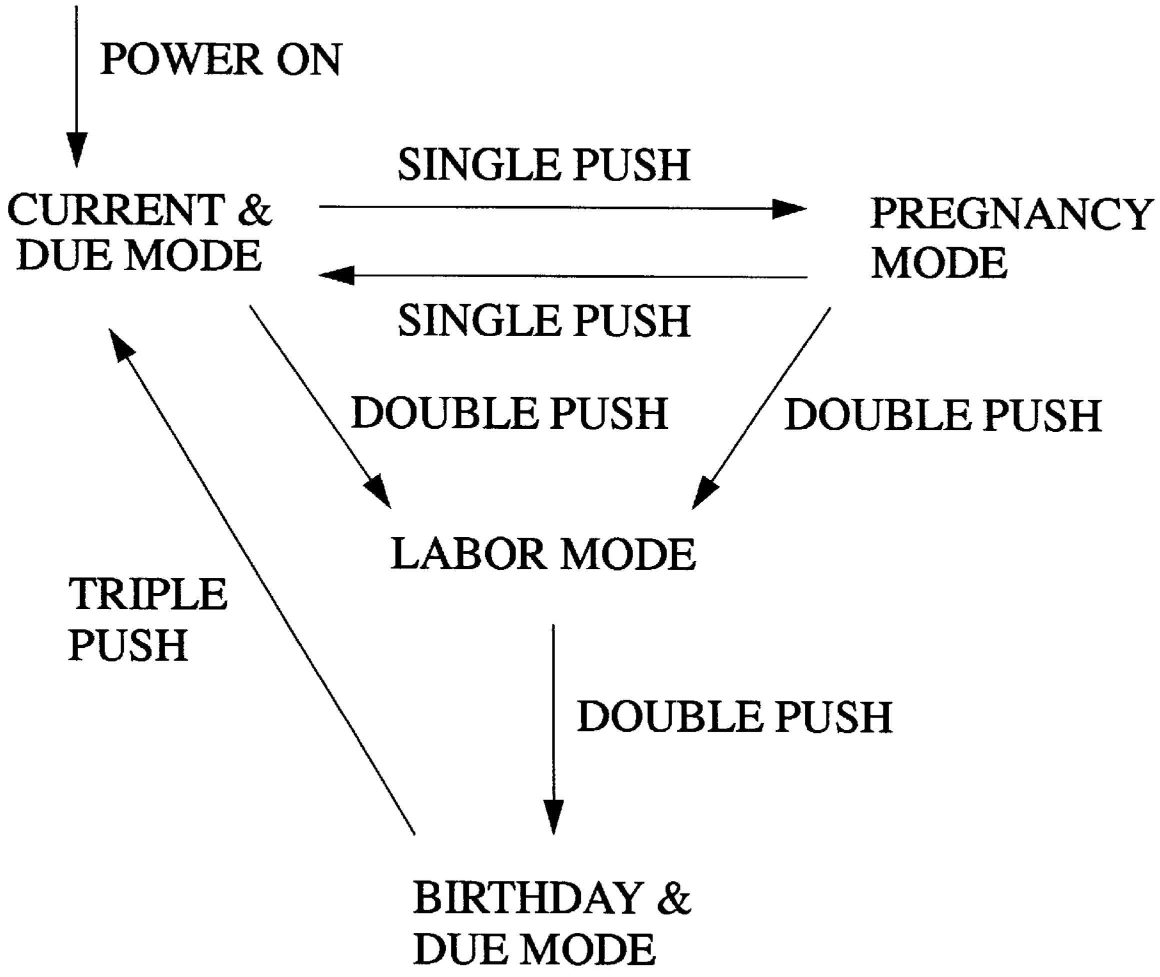
FIG. 17 shows the user-level state transition diagram between the various modes for the "MODE" assigner block (12) of FIG. 3B.

An overall model of the internal workings of the multipurpose pregnancy and labor timing device 120 is shown especially in FIGS. 4B, 4C, and 4D, which depict the so-called "object communication model" of device 120. This set of figures is a graphical model which contains: (a) a number of pre-existing and well-known building blocks hereinafter described, (b) watch control modules, represented as flattened ovals, and (c) stimuli communication, represented by directional lines. Each directional line on the graphical model represents the communication of stimulus from one block/module to another block/module. The name of the stimuli is labeled on or close to the directional line.

The following well-known and pre-existing building blocks generate stimuli for the watch control modules to process: (a) stem switch, which produces a push stimulus each time the user pushes the stem switch hardware, and (b) tick generator, which produces a tick stimulus at a rate which is equal to or greater than a rate of 1 tick per ⅛ second (i.e., at least eight ticks per second).

The stem switch is a simple switch device which, by default, is not pushed (i.e., the stem switch is ready to be pushed). When a stem switch device (reference numerals 144, 142, 146, or 132 in FIG. 2) is pushed by the user, the stem switch device sends a "stem pushed" event to the connected electrical circuit. When the stem switch device is released by the user, the stem switch device does not send any event to the connected electrical circuit. For the multipurpose pregnancy and labor timing device 120, the stem switch is selected from well-known existing components.

The tick generator (reference numeral 134 in FIG. 2) is a simple device that produces a TICK in exactly consistent intervals. The accuracy of the watch time depends upon the consistency of the tick generator. The tick generator is preferably internal to the device 120 and is selected from well-known existing components.

The following well-known and pre-existing building blocks accept stimuli from the watch control modules: (a) multi-tone generator, which produces a single beep, double beep, or birth tones, (b) alphanumeric character display, which causes the hardware to display the requested alphanumeric character string on the display, and (c) light, which causes the illumination light to turn on and off.

The multi-tone generator, shown as reference numeral 138 in FIG. 2, is a simple and well-known device that generates several different tones that are audible to the user. It is assumed that the multi-tone generator chosen for the present invention comes pre-programmed with a variety of songs and/or tones. A simple and pleasant single beep and double beep are preferably included, and preferably a pre-programmed song such as "Happy Birthday" or the like should also be included. For the multipurpose pregnancy and labor timing device 120, the multi-tone generator is selected from well-known existing components.

The alphanumeric character display, shown as reference numeral 140 in FIG. 2, is a simple and well-known device that takes as input the characters to display and displays them for viewing by the user. For purposes of the operational explanation given herein, it is assumed that this display takes character input, but it is well-known by those skilled in the art how to convert characters into segments and/or pixels for presentation to display devices that do not take direct character input. While a well-known alphanumeric LCD display would be adequate for use with the present invention, a well-known 7-segment LCD display would not be acceptable because the various days of the week, etc., could not be properly displayed on such a 7-segment LCD display. For the multipurpose pregnancy and labor timing device 120, the alphanumeric character display is selected from well-known existing components.

The light, reference numeral 148 in FIG. 2, is a simple device that allows the user to see the alphanumeric character display when the device 120 is in the dark. A light with low power consumption is desirable because, during labor, the user may want to turn the light on and leave it on because many birthing facilities are dimly lit. For the multipurpose pregnancy and labor timing device 120, the light is selected from well-known existing components.

There are two other well-known building blocks included within the multipurpose pregnancy and labor timing device 120, namely, (a) persistent memory and (b) a data interface.

The persistent memory is a well-known component and allows the data stored in the device 120 to be saved even when batteries are being changed. The persistent memory is preferably internal to the device 120, and will also be used to store information about each contraction that is recorded by the user when the device 120 is in the "Labor Mode". Some possible well-known components that could be used for constructing the persistent memory are electrically erasable programmable read only memory ("EEPROM") devices as well as fool-proof dual batteries coupled with well-known random access memory ("RAM") devices. For the multipurpose pregnancy and labor timing device 120, the persistent memory is preferably constructed from well-known existing components.

The data interface is preferably a well-known component that allows the persistent memory to be read by an external computer or other electronic equipment. The data interface is preferably internal to the device 120, and is preferably used only by appropriately-trained professionals. One preferred implementation of the data interface is to have the trained professional remove a rear cover from the device 120 and to place a special set of probes on a corresponding set of metal contacts inside the device 120, with the special set of probes then being linked to a well-known personal computer or other well-known electronic equipment. When the device 120 is thus connected to the computer, the computer could read, for example, in a manner well-known to those skilled in the art, the labor contraction information from the device 120. Once the desired information has been extracted by the computer, the probes could then be removed and the rear cover replaced on the device 120.

Each watch control module (a) receives stimuli, (b) carries out the functions for which it is responsible, and (c) generates stimuli. The internal operation of the watch control modules are represented by so-called "Moore" style graphical state models. Each watch control module is explained hereinbelow, and the detailed state model for each watch control module is given in FIG. 3A through FIG. 16, and the action specification logic for each state in each state model is given in the computer program appendix.

The stem switch assigner watch control module will now be described. The stem switch assigner receives a stimulus each and every time the mode stem switch hardware (reference numeral 142 in FIG. 2), the set stem switch hardware (reference numeral 144 in FIG. 2), the increment stem switch hardware (reference numeral 146 in FIG. 2), or the light stem switch hardware (reference numeral 132 in FIG. 2) is pushed. The stem switch assigner also receives a stimulus every one-eighth (⅛) second from the tick counter.

The stem switch assigner is responsible for tracking all of the stem switch pushes such that it can be determined when single, double, and triple pushes have occurred. All stem switch hardware pushes must be processed together because a multi-push sequence on one stem is cancelled whenever other stems are pushed. For example, if the first push of a mode stem switch triple-push has occurred and the set stem switch is pushed, then the mode stem switch triple-push must be started over. The multi-push interval is defined as the amount of time that the user has between pushes before the pushes are considered separate pushes. The multi-push interval is implemented as the time it takes to receive four eighth second ticks (i.e., about one-half second) from the tick counter. This means the multi-push interval is between 0.5 seconds and 0.625 seconds. Whenever the mode stem switch is pushed, the device 120 should "beep". The stimulus of the multi-tone generator hardware occurs from the stem switch assigner.

The stem switch assigner sends stimuli to the mode assigner whenever it determines a single, double, or triple stem push has occurred for the mode stem switch, set stem switch, or increment stem switch. The stem switch assigner sends a stimulus to the multi-tone generator hardware requesting a "beep". The stem switch assigner sends a stimulus to the light hardware whenever the light stem switch is pushed.

The mode assigner watch control module will now be described. The mode assigner receives a stimulus each time the stem switch assigner determines that a single, double, or triple stem push has occurred. The mode assigner is responsible for managing the movement of the device 120 through each of the various mode states, i.e., the "CURRENT & DUE MODE", the "PREGNANCY MODE", the "LABOR MODE", and the "BIRTHDAY & DUE MODE", as depicted in the user-level state transition diagram shown in FIG. 17. The mode assigner sends activation and inactivation stimuli to the current & due mode assigner, the pregnancy mode assigner, the labor mode assigner, and the birthday & due mode assigner. The mode assigner also forwards the single, double, and triple stem pushes to the various mode assigners.

The preferred four user-level-visible modes of the mode assigner can now be described.

In the "CURRENT & DUE MODE", the device 120 displays the current date, current time, current day of week, and the expected due date for the child. This mode also allows the user to set the current date, current time, and expected due date. The current day of week is calculated from the current date and cannot be set directly by the user. Successive pressings of the set stem switch allow the user to access and change the various digits in the displays of device 120, while successive pressings of the increment stem switch change each digit (modulo the highest permissible value for the current digit being changed).

In the "PREGNANCY MODE", the device 120 displays the time elapsed in the pregnancy and the time remaining in the pregnancy. This mode does not allow the user to change any values, and all pressings of the set stem switch and increment stem switch are ignored. The elapsed time and the time remaining in the pregnancy are calculated based upon the current date and time and the expected due date and time, with the expected due time on the expected due date preferably being chosen as noon on the expected due date. The elapsed time in the pregnancy is calculated based on an assumed length of pregnancy being 40 weeks, with conception date and time thus being assumed to occur 40 weeks prior to the expected due date and time, and with the elapsed time in the pregnancy being calculated by subtracting the calculated conception date and time from the current date and time. Similarly, the time remaining in the pregnancy is calculated by subtracting the current date and time from the expected due date and time. The time remaining in the pregnancy thus counts down to zero, at which point the absolute value of the calculated time remaining is then displayed to indicate the amount by which the birth is overdue.

In the "LABOR MODE", the device 120 displays the count of contractions, the current time, the time interval between the last contraction and the current contraction, and the duration of the current contraction. When this mode is entered, the count of contractions, the contraction interval time, and the contraction duration time are all initialized to zero. If the user pushes the increment stem switch, the contraction counter will then increment (to one) and the contraction duration time will begin counting up. When the user pushes the increment stem switch again, then the contraction duration time will freeze at its then-current value and the contraction interval time will begin counting up. When the user pushes the increment stem switch again, the contraction interval time will freeze at its then-current value, the contraction counter will increment by one, and the contraction duration time will be reset to zero and will then begin counting up. When the user pushes the increment stem switch again, the contraction duration time will freeze at its then-current value and the contraction interval time will be reset to zero and will then begin counting up. The counting of contractions, their duration, and the interval between contractions continues with successive pressings of the increment stem switch. The starting time and ending time of the most recent 999 contractions are stored in the persistent memory, and this information may be read out via the data interface. It should be understood that the starting and ending times for a greater or lesser number of contractions may be stored in the persistent memory depending on the particular size of persistent memory selected for a given implementation. If the user double-pushes the set stem switch, then the contraction counter and the timers will be cleared to zero.

In the "BIRTHDAY & DUE MODE", the device 120 displays the actual birth date, the actual birth time, the actual birth day of week, and the original expected due date. The actual birth date and actual birth time are set by copying the current date and current time when this mode is entered. The actual birth day of week is calculated from the actual birth date and cannot be set by the user. The birth date and birth time are "frozen" for posterity and do not count up or down.

The current & due mode assigner watch control module will now be described. The current & due mode assigner receives activation, inactivation, single stem push, and double stem push stimuli from the mode assigner.

The current & due mode assigner is responsible for setting up the content and format of each alpha-numeric display such that the device 120 displays the information heretofore described as being shown in the "CURRENT & DUE MODE". The current & due mode assigner is also responsible for setting the current date, the current time, and the expected due date in response to the user's set stem pushes and increment stem pushes. At the end of setting all digits of the current date, the current & due mode assigner is responsible for generating a "double beep". The "double beep" is also generated at the completion of setting the current time and the expected due date digits.

The current & due mode assigner sends "set" and "run" stimuli to the current date, the current time, and due date modules. In addition, the current & due mode assigner directly changes the current date, current time, and expected due date data as well as the display content and format setup. Finally, the current & due mode assigner sends a stimulus to the multi-tone generator hardware requesting a "double beep".

The pregnancy mode assigner watch control module will now be described. The pregnancy mode assigner receives activation and inactivation stimuli from the mode assigner. The pregnancy mode assigner is responsible for setting up the content and format of each alpha-numeric display such that device 120 displays the information heretofore described as being shown in the "PREGNANCY MODE". The pregnancy mode assigner directly changes the display content and format setup.

The labor mode assigner watch control module will now be described. The labor mode assigner receives activation, inactivation, single stem push, and double stem push stimuli from the mode assigner.

The labor mode assigner is responsible for setting up the content and format of each alpha-numeric display such that device 120 displays the information heretofore described as being shown in the "LABOR MODE". The labor mode assigner must manage the user's increment stem switch pushes which indicate the start and stop of a contraction. The contraction counter is managed, the contraction duration time is managed, and the contraction interval time is managed by the labor mode assigner. Also, the labor mode assigner manages the storage of the start time and stop time of the last 999 contractions (or some greater or lesser number of contractions, depending on the implementation) in the memory of the watch. The labor mode assigner must also manage the user's set stem switch double pushes which indicate the desire to clear the stored contraction data.

The labor mode assigner sends halt and run stimuli to the contraction duration time and contraction interval timer. The labor mode assigner sends clear and increment stimuli to the contraction counter. In addition, the labor mode assigner directly changes the display content and format setup.

The birthday & due mode assigner watch control module will now be described. The birthday & due mode assigner receives activation and inactivation stimuli from the mode assigner. The birthday & due mode assigner is responsible for setting up the content and format of each alpha-numeric display such that device 120 displays the information heretofore described as being shown in the "BIRTHDAY & DUE MODE". The birthday & due mode assigner directly changes the display content and format setup.

The tick counter watch control module will now be described. The tick counter receives tick stimuli from the tick hardware. The tick counter is responsible for counting ticks, such that it can generate one-eighth (1/8) second ticks, one-half (1/2) second ticks, and full second ticks. The tick counter sends half-second tick and full-second tick stimuli to all date clocks and time clocks. The tick counter also sends one-eighth second ticks to the stem switch assigner.

The date clock watch control module will now be described. The date clock receives half-second tick and full-second tick stimuli from the tick counter. The date clock receives full day tick stimuli from the time clock. The date clock is responsible for incrementing the date based on full day tick stimuli from the time clock. The date clock must take into account the varying number of days in each month including 29 days in February for each leap year. The date clock is responsible for flashing the digit that is currently being set, based on the half-second ticks and full second ticks. The flashing consists of a half-second on and a half-second off. The date clock sends display stimuli to the related display.

The time clock watch control module will now be described. The time clock receives half-second tick and full-second tick stimuli from the tick counter. The time clock is responsible for incrementing the time based on full-second tick stimuli from the tick counter. The time clock is responsible for flashing the digit that is currently being set, based on the half-second ticks and full-second ticks. The flashing consists of a half-second on and a half-second off. The time clock sends display stimuli to the related display. The time clock also sends full day tick stimuli to the date clock whenever midnight occurs.

The contraction counter watch control module will now be described. The contraction counter receives clear, start contraction, and end contraction stimuli from the labor mode assigner. The contraction counter is responsible for incrementing the contraction count and for recording the start time and end time of the last 999 contractions (or some greater or lesser number of contractions, depending on the implementation) in the memory of device 120. The contraction counter is responsible for clearing all recorded contraction data from the memory of device 120 when the clear stimuli is received. The contraction counter sends display stimuli to the related display.

The display watch control module will now be described. The display receives display stimuli from the date clocks, time clocks, and contraction counter. The display is responsible for forwarding the display stimuli on to the appropriate display hardware. The display sends display stimuli to the appropriate display hardware.

A preferred embodiment of the software commands (the "action specification logic") to control the internal operation of the multipurpose pregnancy and labor timing device 120 is provided with this application as a microfiche appendix.

Although the present invention has been described and illustrated with respect to a preferred embodiment and a preferred use therefor, it is not to be so limited since modifications and changes can be made therein which are within the full intended scope of the invention.

We claim:

1. A multipurpose pregnancy and labor timing watch, said watch comprising:

(a) output means for displaying a plurality of information, said output means including a plurality of alphanumeric displays and said output means having a plurality of selectively-chosen display modes; said information including:

i. a current time, a current date, and a current weekday;

ii. an expected due date for birth of a child;

iii. an elapsed time since an estimated conception of the child;

iv. an estimated time until the expected due date for birth of the child;

v. a count of contractions during birth of the child;

vi. a time interval between contractions during birth of the child;

vii. a duration of contractions during birth of the child;

viii. a recorded birth time, birth date, and birth weekday;

said plurality of display modes including:

i. a first mode in which said output means simultaneously displays the current time, the current date, the current weekday, and the expected due date for birth of the child;

ii. a second mode in which said output means simultaneously displays the elapsed time since the estimated conception of the child and the estimated time until the expected due date for birth of the child;

iii. a third mode in which said output means simultaneously displays the count of contractions during birth of the child, the time interval between contractions during birth of the child, the duration of contractions during birth of the child, and the current time;

iv. a fourth mode in which said output means simultaneously displays the recorded birth time, birth date, and birth weekday;

(b) nonvolatile memory means for storing said at least some of said information;

(c) processor control means for controlling said output means, for storing at least some of said information in said nonvolatile memory means, and for calculating other of said information from said stored at least some of said information;

(d) mode selection means for selectively choosing one of said plurality of display modes for said output means;

(e) data initialization means for initializing said watch for said stored some of said information;

said mode selection means, when said fourth mode is entered, causing the recorded birth time, birth date, and birth weekday to be freezingly preserved by said processor means from the current time, the current date, and the current weekday, respectively.

2. The multipurpose pregnancy and labor timing watch as recited in claim 1, in which said watch additionally includes tone generator means for playing a preselected song when said fourth mode is entered.

* * * * *